(12) United States Patent
Yang et al.

(10) Patent No.: US 8,148,423 B2
(45) Date of Patent: Apr. 3, 2012

(54) FLUOROPHORE COMPOUNDS

(75) Inventors: Dan Yang, Hong Kong (HK); Tao Peng, Hong Kong (HK)

(73) Assignees: Versitech Limited, Hong Kong (CN); Morningside Ventures Limited, Hong Kong (CN)

( * ) Notice: Subject to any disclaimer, the term of this patent is extended or adjusted under 35 U.S.C. 154(b) by 426 days.

(21) Appl. No.: 12/417,640

(22) Filed: Apr. 3, 2009

(65) Prior Publication Data

US 2009/0253143 A1    Oct. 8, 2009

Related U.S. Application Data

(60) Provisional application No. 61/041,923, filed on Apr. 3, 2008.

(51) Int. Cl.
*A61K 31/352* (2006.01)
*C07D 311/78* (2006.01)
*C07D 407/02* (2006.01)

(52) U.S. Cl. ........ 514/454; 549/263; 549/265; 514/449; 514/451

(58) Field of Classification Search ................. 549/263, 549/265; 514/449, 451, 454
See application file for complete search history.

(56) References Cited

U.S. PATENT DOCUMENTS

| 5,227,487 A | * | 7/1993 | Haugland et al. | ................ 546/15 |
| 5,442,045 A | * | 8/1995 | Haugland et al. | .......... 530/391.3 |
| 5,723,218 A | * | 3/1998 | Haugland et al. | ............. 428/402 |

OTHER PUBLICATIONS

Ioffe et al (1965): STN International HCAPLUS database, (Columbus, Ohio), Accession No. 1965:91503.*
Haugland et al (1993): STN International HCAPLUS database, (Columbus, Ohio), Accession No. 1993:652145.*

* cited by examiner

*Primary Examiner* — Golam M M Shameem
(74) *Attorney, Agent, or Firm* — Saliwanchik, Lloyd & Eisenschenk

(57) ABSTRACT

Provided herein are fluorophore compounds including rhodol and rhodamine compounds which can be used as fluorescent labels and/or fluorogenic probes and methods of making same. Provided also herein are methods that can be used to track, measure, detect, or screen biological species such as protein, DNA, enzyme, antibody, organelle, cell, tissue, drug, hormone, nucleotide, nucleic acid, polysaccharide or lipid in living organisms. Specifically, the methods include the steps of contacting any of the fluorophore compounds, rhodol compounds and rhodamine compounds disclosed herein with the biological species to form one or more fluorescent compounds, and measuring fluorescence properties of the fluorescent compounds. Provided also herein are high-throughput screening fluorescent methods for detecting or screening biological species.

8 Claims, No Drawings

FLUOROPHORE COMPOUNDS

PRIOR RELATED APPLICATIONS

This application claims priority to U.S. Provisional Patent Application Ser. No. 61/041,923, filed Apr. 3, 2008, which is incorporated herein by reference in its entirety.

FIELD

Provided herein are fluorophore compounds. Specifically, provided herein are fluorophore compounds including rhodol and rhodamine fluorophores which can be used as fluorescent labels and/or fluorogenic probes. Provided also herein are new and versatile methods for making the fluorophore compounds disclosed herein. Provided also herein are methods of tracking, measuring, detecting, or screening biological species.

BACKGROUND

Fluorescence technology is enjoying ever-increasing interest from many areas of science including chemistry and biology. In certain instances, fluorescent molecules can be used to detect the presence or absence of analytes or chemicals in food and environmental samples. Some sensitive and quantitative fluorescence detection devices are required for in vitro biochemical assays such as DNA sequencing and blood glucose quantification. In some instances, fluorescent probes having suitable photochemical properties can be used for tracing molecular and physiological events in living cells as well as for high-throughput screenings. In general, fluorescence technology is simpler and can provide higher sensitivity and more molecular information than other types of optical measurements. Fluorescence measurements are generally highly sensitive because of the low level of fluorescence background generally found in most chemical and biological samples. Along with the recent advances in fluorescence instrumentation such as confocal and multi-photo fluorescence microscopies, three-dimensional imaging of cellular events and biological species dynamics have become possible in real-time.

Despite of the above-mentioned advantages, the feasibility of using fluorescence technology for a particular application can often be limited by the availability of appropriate fluorescent molecules. Fluorescent molecules generally include fluorescent label (or fluorescent tracer) molecules and fluorogenic probe (or fluorogenic sensor) molecules, both of which differ in their fluorescence properties. In general, the fluorescence of fluorescent label molecules always keeps in "on" state. The fluorescent label molecules may be used to track biological species. On the contrary, the fluorescence properties of the fluorogenic probe molecules can be changed by bonding to or reacting with certain analytes or chemicals. Therefore, the fluorogenic probe molecules can be used to trace, measure, detect or screen various analytes or chemicals that bond or react with the fluorogenic probe molecules.

When used as fluorescent labels or fluorescent dyes, the fluorescent label molecules need to chemically react with a biologically active target, such as a protein, DNA, enzyme, antibody, organelle, cell, tissue, drug, hormone, nucleotide, nucleic acid, polysaccharide, lipid or other biomolecules, to yield a fluorescent derivative of the target. The number of available fluorescent label molecules that can react with a biologically active target is generally limited. Reactive fluorescein and rhodamine derivatives have been by far the most widely used fluorescent label molecules because they can be suitably excited by commonly used light sources, such as the argon laser (488 nm and 514 nm lines) and the mercury arc lamp (546 nm line). However, they have some undesirable properties that may preclude them to be used in some useful applications. For example, fluorescein derivatives can be photo-bleached in a relative high rate and may show pH dependent absorptions that lead to significantly reduced fluorescence at or below physiological pH value 7. On the other hand, rhodamine derivatives, which are relatively photostable and exhibit pH insensitive fluorescence compared to fluorescein derivatives, show much lower quantum yields in aqueous solution and further decreases in quantum yield when conjugated with proteins. Furthermore, the low water solubility of rhodamine derivatives and conjugates thereof presents difficulties for the preparation and use of fluorescent label molecules comprising rhodamine derivatives.

In view of the undesirable properties of the fluorescein and rhodamine derivatives mentioned above, there is a need for new fluorescent label molecules that have improved properties over those of fluorescein and rhodamine derivatives. Some rhodol or fluorescein derivatives, such as those described in Ioffe et al., *J. Org. Chem. USSR* 1965, 1, 326-336; Reynolds, G. A., U.S. Pat. No. 3,932,415; Lee et al., *Cytometry* 1989, 10, 151-164; Haugland et al., U.S. Pat. No. 5,227,487; Whitaker et al., *Anal. Biochem.* 1992, 207, 267-279, may be used as alternative fluorescent label molecules because they generally have the desirable properties of fluorescein and rhodamine. For example, they have desirable absorption properties, low sensitivity of fluorescence to pH in the physiological range and solvent polarity, high extinction coefficients, high quantum yields, high photostability, and high solubility in a variety of solvents.

Despite their desirable properties, the applications of rhodol fluorescent dyes as fluorescent labels or fluorogenic probes are seldom reported in the literature, which may be due to difficulties of synthesizing rhodol compounds. In general, a key synthetic step of making a rhodol fluorophore is condensing a substituted or unsubstituted resorcinol with a substituted or unsubstituted 6-acyl-3-aminophenol in the presence of a Lewis acid catalyst such as zinc chloride or a dehydrating acid. Alternatively, the rhodol fluorophore can be prepared by condensing a substituted or unsubstituted amino phenol with a substituted or unsubstituted 4-acyl-resorcinol in the presence of a Lewis acid catalyst. The general synthetic methods mentioned above generally suffer from low yield and tedious purification work. Therefore, there is a need for developing a more efficient synthetic method for making fluorophore compounds such as rhodol fluorophores.

Recently, the developments of fluorogenic probes for different targets have encountered a bottleneck. It may be due to the fact that most currently available fluorogenic probes are developed empirically, but not rationally, which can hamper the design of new fluorogenic probes. Although there have been some reported methods of applying theoretical approaches to the design of fluorogenic probes, these are still far from enough. Another effective approach involves combinatorial synthesis of libraries of fluorogenic probe molecules. Rhodol fluorophores are suitable candidates in a fluorogenic probe library because of their advantageous photophysical properties as stated above. Therefore, there is also a need for a library of fluorophore compounds including rhodol fluorophores that can be easily developed by the new and efficient synthetic methods for making fluorophore compounds disclosed herein.

SUMMARY

Provided herein are fluorophore compounds such as rhodol and rhodamine fluorophores that can be used as fluorescent labels and/or fluorogenic probes for tracking, measuring, detecting or screening biological species and method of making the same.

In one aspect, provided herein are methods of preparing a fluorophore compound having formula (III) or (VI):

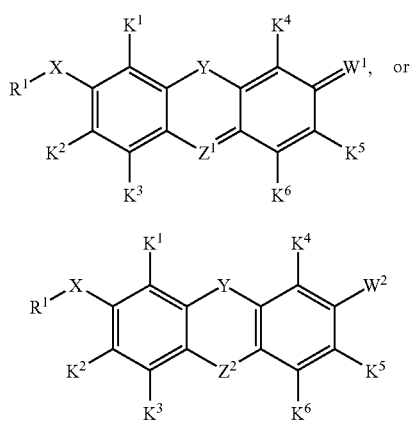

or a salt thereof, the method comprising the steps of:
(a) reacting respectively formula (I) or (IV):

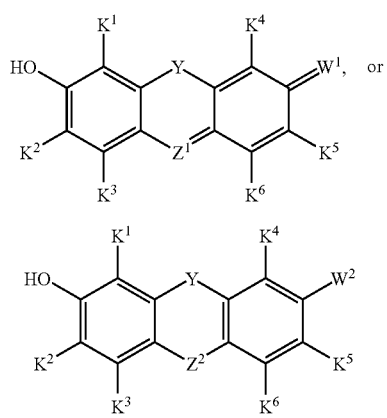

with a hydroxy activating agent having formula B-X' to yield respectively an intermediate (II) or (V):

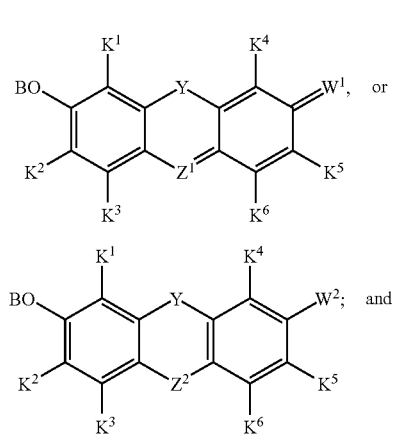

(b) coupling the intermediate (II) or (V) with a nucleophile having formula $HXR^1$ in the presence of a palladium catalyst to form the fluorophore compound of formula (III) or (VI) respectively, wherein OB is a hydroxy activating group;
$W^1$ is O or S;
$W^2$ is O-A, S-A or $NR^3R^4$;
X is $NR^2$, O or S;
Y is O, S, Se, $NR^5$ or $CR^6R^7$;
$Z^1$ is $CR^8$ or N;
$Z^2$ is $CR^9R^{10}$ or $NR^{11}$;
A is H, alkyl, alkenyl, alkynyl, alkoxyalkyl, heteroalkyl, cycloalkyl, cycloalkenyl, cycloalkynyl, heterocyclyl, aminoalkyl, aryl, alkaryl, arylalkyl, carboxyalkyl, alkoxycarbonyl, acyl, aminocarbonyl, a hydroxy protecting group or a reactive functional group;
each of $R^1$, $R^2$, $R^3$, $R^4$, $R^5$, $R^6$, $R^7$, $R^9$, $R^{10}$ and $R^{11}$ is independently H, alkyl, alkenyl, alkynyl, alkoxyalkyl, heteroalkyl, cycloalkyl, cycloalkenyl, cycloalkynyl, heterocyclyl, aminoalkyl, aryl, alkaryl, arylalkyl, alkyloxy, carboxyalkyl, alkylamido, alkoxyamido, sulfonylaryl, acyl or a reactive functional group, or $CR^9R^{10}$ is a substituted 2-carboxyphenyl-C group having formula (VII) or (VIIa):

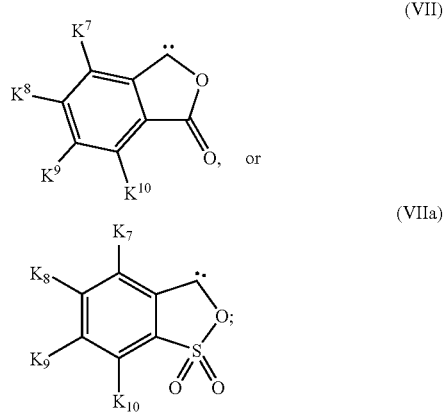

$R^8$ is H, alkyl, alkenyl, alkynyl, alkoxyalkyl, heteroalkyl, cycloalkyl, cycloalkenyl, cycloalkynyl, heterocyclyl, aminoalkyl, aryl, alkaryl, arylalkyl, alkyloxy, carboxyalkyl, alkylamido, alkoxyamido, sulfonylaryl, acyl or a reactive functional group, or has formula (VIIb) or (VIIc):

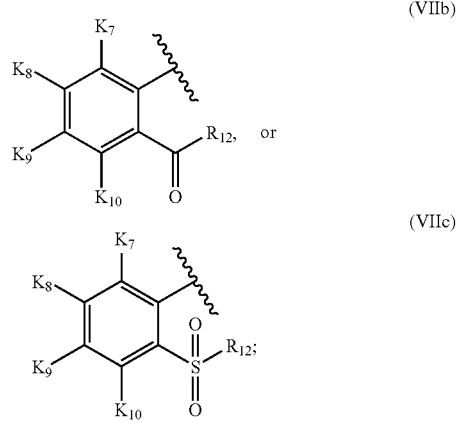

each of $K^1$, $K^2$, $K^3$, $K^4$, $K^5$, $K^6$, $K^7$, $K^8$, $K^9$ and $K^{10}$ is independently H, halo, alkyl, halogenated alkyl, heteroalkyl, alkenyl, alkynyl, aryl, aralkyl, alkaryl, heterocyclyl, cycloalkyl, cycloalkenyl, cycloalkynyl, hydroxyalkyl, aminoalkyl, amino, alkylamino, arylamino, dialkylamino, alkylarylamino, diarylamino, acylamino, hydroxy, thio, thioalkyl, alkoxy, alkylthio, alkoxyalkyl, aryloxy, arylalkoxy, acyloxy, cyano, nitro, sulfhydryl, carbamoyl, trifluoromethyl, phenoxy, benzyloxy, sulfonyl, phosphonyl, sulfonate ester, phosphate ester, —C(=O)—P¹ or —C(=O)-Q-P²;

each of $P^1$ and $P^2$ is independently hydrogen, halo, alkoxy, hydroxy, thio, alkyl, alkenyl, alkynyl, cycloalkyl, cycloalkenyl, cycloalkynyl, aryl, alkaryl, arylalkyl, carbamate, amino, alkylamino, arylamino, dialkylamino, alkylarylamino, diarylamino, alkylthio, heteroalkyl, or heterocyclyl having from 3 to 7 ring atoms; and Q is alkylene, alkenylene, alkynylene, arylene, aralkylene or alkarylene.

In some embodiments, the fluorophore compound is a rhodol fluorophore having formula (VIII):

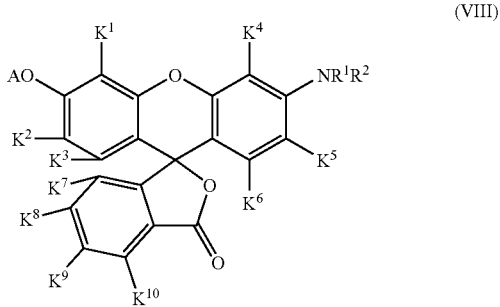

(VIII)

or a salt thereof, wherein A, $R^1$, $R^2$, $K^1$, $K^2$, $K^3$, $K^4$, $K^5$, $K^6$, $K^7$, $K^8$, $K^9$ and $K^{10}$ are as disclosed herein.

In other embodiments, the fluorophore compound is a rhodol fluorophore having formula (IX):

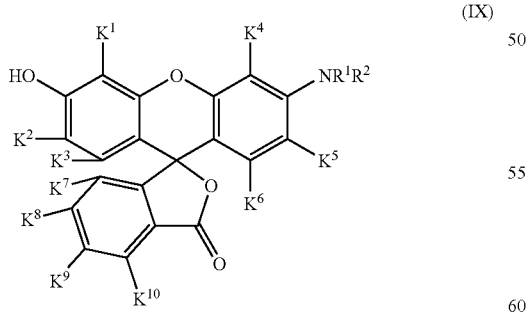

(IX)

or a salt thereof, wherein $R^1$, $R^2$, $K^1$, $K^2$, $K^3$, $K^4$, $K^5$, $K^6$, $K^7$, $K^8$, $K^9$ and $K^{10}$ are as disclosed herein.

In other embodiments, the fluorophore compound is a rhodamine fluorophore having formula (XIII):

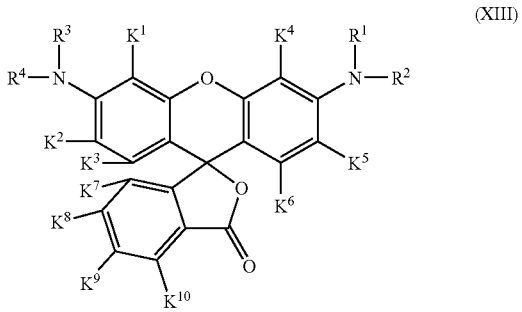

(XIII)

or a salt thereof, wherein each of $R^1$, $R^2$, $R^3$, $R^4$, $K^1$, $K^2$, $K^3$, $K^4$, $K^5$, $K^6$, $K^7$, $K^8$, $K^9$ and $K^{10}$ are as disclosed herein. In other embodiments, $R^1$ and $R^3$ are the same and $R^2$ and $R^4$ are the same.

In some embodiments, the hydroxy activating group is methanesulfonate, p-toluenesulfonate, trifluoromethanesulfonate, nonafluorobutanesulfonate, p-nitrobenzoate, or phosphonate. In other embodiments, the hydroxy activating agent is mesyl halide, triflyl halide, tosyl halide, nonflyl halide, mesyl anhydride, triflyl anhydride, tosyl anhydride, nonflyl anhydride, or a combination thereof. In further embodiments, B is a sulfonyl, carboxyl or phosphonyl. In still further embodiments, B is a sulfonyl selected from mesyl, triflyl, tosyl or nonflyl.

In certain embodiments, X of the nucleophile is $NR^2$, wherein each of $R^1$ and $R^2$ is independently H, alkyl, alkenyl, alkynyl, alkoxyalkyl, heteroalkyl, cycloalkyl, cycloalkenyl, cycloalkynyl, heterocyclyl, aminoalkyl, aryl, alkaryl, arylalkyl, alkyloxy, carboxyalkyl, alkylamido, alkoxyamido, sulfonylaryl, acyl or a reactive functional group.

In some embodiments, the palladium catalyst comprises at least a palladium source. In other embodiments, the palladium source is palladium acetate, tris(dibenzylideneacetone)dipalladium or a combination thereof. In further embodiments, the palladium catalyst comprises at least a phosphine ligand or a carbene ligand. In still further embodiments, the phosphine ligand is rac-2,2'-bis(diphenylphosphino)-1,1'-binaphthalene (BINAP), 1,1'-bis(diphenylphosphino)ferrocene (dppf), 2-(dicyclohexylphosphino)biphenyl, tricyclohexylphosphine, triphenylphosphine, tri-t-butylphosphine, 9,9-dimethyl-4,5-bis(diphenylphosphino)xanthene (Xantphos), 2-(di-t-butylphosphino)biphenyl, or rac-2-(di-t-butylphosphino)-1,1'-binaphthyl.

In another aspect, provided herein are rhodol compounds having formula (VIII):

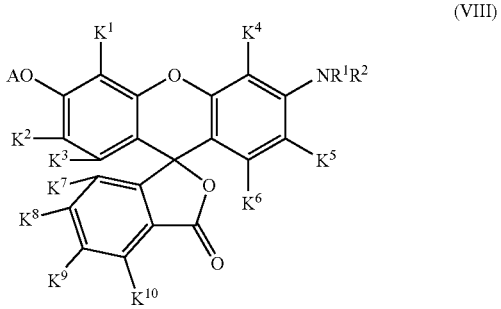

(VIII)

or a salt thereof, wherein A, $R^1$, $R^2$, $K^1$, $K^2$, $K^3$, $K^4$, $K^5$, $K^6$, $K^7$, $K^8$, $K^9$ and $K^{10}$ are as disclosed herein, with the proviso that at least one of $R^1$ and $R^2$ comprises a reactive functional group.

In another aspect, provided herein are rhodamine compounds having formula (XIII):

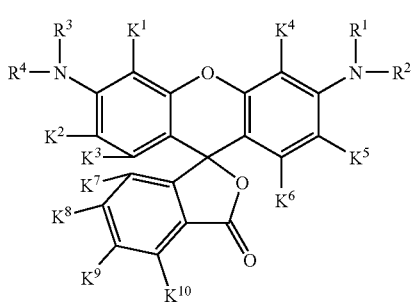

(XIII)

or a salt thereof,
wherein each of $R^1$, $R^2$, $R^3$, $R^4$, $K^1$, $K^2$, $K^3$, $K^4$, $K^5$, $K^6$, $K^7$, $K^8$, $K^9$ and $K^{10}$ is as disclosed herein, with the proviso that at least one of $R^1$, $R^2$, $R^3$ and $R^4$ comprises a reactive functional group. In other embodiments, $R^1$ and $R^3$ are the same and $R^2$ and $R^4$ are the same.

In some embodiments, each of $K^1$, $K^2$, $K^3$, $K^4$, $K^5$, $K^6$, $K^7$, $K^8$, $K^9$ and $K^{10}$ is independently H. In other embodiments, each of $R^1$ and $R^2$ is alkyl. In further embodiments, each of $K^1$, $K^3$, $K^4$, $K^6$, $K^7$, $K^8$, $K^9$ and $K^{10}$ is independently H; and each of $K^2$ and $K^5$ is independently chlorine or fluorine. In still further embodiments, each of $R^1$ and $R^2$ is methyl, ethyl, propyl or butyl. In still further embodiments, $R^1$ is H; and $R^2$ is alkyl.

In certain embodiments, the hydroxy protecting group is benzyloxycarbonyl, 4-nitrobenzyloxycarbonyl, 4-bromobenzyloxycarbonyl, 4-methoxybenzyloxycarbonyl, methoxycarbonyl, tert-butoxycarbonyl, isopropoxycarbonyl, diphenylmethoxycarbonyl, 2,2,2-trichloroethoxycarbonyl, 2-(trimethylsilyl)ethoxycarbonyl, 2-furfuryloxycarbonyl, allyloxycarbonyl, acetyl, formyl, chloroacetyl, trifluoroacetyl, methoxyacetyl, phenoxyacetyl, benzoyl, methyl, t-butyl, 2,2,2-trichloroethyl, 2-trimethylsilyl ethyl, 1,1-dimethyl-2-propenyl, 3-methyl-3-butenyl, allyl, benzyl, para-methoxybenzyldiphenylmethyl, triphenylmethyl (trityl), tetrahydrofuryl, methoxymethyl, methylthiomethyl, benzyloxymethyl, 2,2,2-triehloroethoxymethyl, 2-(trimethylsilyl) ethoxymethyl, methanesulfonyl, p-toluenesulfonyl, trimethylsilyl, triethylsilyl or triisopropylsilyl.

In some embodiments, the reactive functional group is derived from acrylamide, acyl azide, acyl halide, nitrile, aldehyde, ketone, alkyl halide, alkyl sulfonate, anhydride, aryl halide, alkyne, alcohol, amine, carboxylic acid, carbodiimide, diazoalkane, epoxide, haloacetamide, hydroxylamine, hydrazine, imido ester, isothiocyanate, maleimide, sulfonate ester or sulfonyl halide by removing a hydrogen or a monovalent atom or group such as OH or halide.

In another aspect, provided herein are methods for tracking, detecting, measuring or screening a biological species, wherein the method comprises the steps of:
a) contacting a fluorophore compound disclosed herein (e.g., rhodol and rhodamine compounds) with the biological species to form a fluorescent compound; and
b) measuring fluorescence properties of the fluorescent compound.

In another aspect, provided herein are high-throughput screening fluorescent methods for tracking or detecting a biological species in samples, wherein the high-throughput method comprises the steps of:

a) contacting a fluorophore compound disclosed herein (e.g., rhodol and rhodamine compounds) with the samples to form one or more fluorescent compounds; and
b) measuring fluorescence properties of the fluorescent compounds to determine the amount of the biological species in the samples.

In some embodiments, the biological species comprise protein, DNA, enzyme, antibody, organelle, cell, tissue, drug, hormone, nucleotide, nucleic acid, polysaccharide or lipid from an animal. In further embodiments, the animal is human.

Definitions

To facilitate the understanding of the subject matter disclosed herein, a number of terms, abbreviations or other shorthand as used herein are defined below. Any term, abbreviation or shorthand not defined is understood to have the ordinary meaning used by a skilled artisan contemporaneous with the submission of this application.

"Amino" refers to a primary, secondary, or tertiary amine which may be optionally substituted. Specifically included are secondary or tertiary amine nitrogen atoms which are members of a heterocyclic ring. Also specifically included, for example, are secondary or tertiary amino groups substituted by an acyl moiety. Some non-limiting examples of amino group include —$NR_6R_7$ wherein each of $R_6$ and $R_7$ is independently hydrogen, alkyl, aryl, aralkyl, alkaryl, cycloalkyl, acyl, heteroalkyl, heteroaryl or heterocyclyl.

"Alkyl" refers to a fully saturated acyclic monovalent radical containing carbon and hydrogen, and which may be branched or a straight chain. In some embodiments, alkyl contains from about 1 to about 25 carbon atoms. Examples of alkyl groups are methyl, ethyl, n-propyl, isopropyl, n-butyl, t-butyl, n-heptyl, n-hexyl, n-octyl, and n-decyl. "Lower alkyl" refers to an alkyl radical of one to six carbon atoms, as exemplified by methyl, ethyl, n-butyl, i-butyl, t-butyl, isoamyl, n-pentyl, and isopentyl.

"Heteroalkyl" refers to an alkyl group having one or more of the carbon atoms within the alkyl group substituted by a heteroatom such as O, S and N. In some embodiments, the heteroalkyl group comprises one or more O atoms. In other embodiments, the heteroalkyl group comprises one or more S atoms. In further embodiments, the heteroalkyl group comprises one or more aminylene groups. In certain embodiments, the heteroalkyl group comprises two or more O, S, aminylene or a combination thereof.

"Alkenyl" or "alkenylene" respectively refers to a monovalent or divalent hydrocarbyl radical which has at least one double bond. The alkenyl or alkenylene group may be cyclic, branched acyclic or straight acyclic. In some embodiments, the alkenyl or alkenylene group contains only one double bond. In other embodiments, the alkenyl or alkenylene group contains two or more double bonds. In further embodiments, the alkenyl or alkenylene group can be a lower alkenyl or alkenylene containing from two to eight carbon atoms in the principal chain. In further embodiments, the alkenyl or alkenylene group can have one double bond and up to 25 carbon atoms, as exemplified by ethenyl, propenyl, isopropenyl, butenyl, isobutenyl, hexenyl, and the like.

"Alkynyl" or "alkynylene" respectively refers to a monovalent or divalent hydrocarbyl radical which has at least a triple bond. In some embodiments, the alkynyl or alkynylene group contains only one triple bond. In other embodiments, the alkynyl or alkynylene group contains two or more triple bonds. In further embodiments, the alkynyl or alkynylene group can be a lower alkynyl or alkynylene containing from two to eight carbon atoms in the principal chain. In further embodiments, the alkynyl or alkynylene group can have one triple bond and up to 20 carbon atoms, as exemplified by ethynyl, propynyl, isopropynyl, butynyl, isobutynyl, hexynyl, and the like.

"Aromatic" or "aromatic group" refers to aryl or heteroaryl.

"Aryl" refers to optionally substituted carbocyclic aromatic groups. In some embodiments, the aryl group includes a monocyclic or bicyclic group containing from 6 to 12 carbon atoms in the ring portion, such as phenyl, biphenyl, naphthyl, substituted phenyl, substituted biphenyl or substituted naphthyl. In other embodiments, the aryl group is phenyl or substituted phenyl.

"Aralkyl" refers to an alkyl group which is substituted with an aryl group. Some non-limiting examples of aralkyl include benzyl and phenethyl.

"Alkaryl" refers to an aryl group which is substituted with an alkyl group. Some non-limiting examples of alkaryl include methylphenyl and methylnaphthyl.

"Acyl" refers to a monovalent group of the formula —C(=O)H, —C(=O)-alkyl, —C(=O)-aryl, —C(=O)-aralkyl, or —C(=O)-alkaryl.

"Halogen" or "halo" refers to fluorine, chlorine, bromine and iodine.

"Heteroatom" refers to atoms other than carbon and hydrogen.

"Heterocyclo" or "heterocyclyl" refers to optionally substituted, fully saturated or unsaturated, monocyclic or bicyclic, aromatic or non-aromatic groups having at least one heteroatom, such as O, S, N, B and P, in at least one ring. The aromatic heterocyclyl (i.e., heteroaryl) group can have 1 or 2 oxygen atoms, 1 or 2 sulfur atoms, and/or 1 to 4 nitrogen atoms in the ring, and may be bonded to the remainder of the molecule through a carbon or heteroatom. Some non-limiting examples of heteroaryl include furyl, thienyl, thiazolyl, pyridyl, oxazolyl, pyrrolyl, indolyl, quinolinyl, or isoquinolinyl and the like.

"Hydrocarbon" or "hydrocarbyl" refers to organic compounds or radicals consisting exclusively of the elements carbon and hydrogen. Hydrocarbyl includes alkyl, alkenyl, alkynyl, and aryl moieties. Hydrocarbyl also includes alkyl, alkenyl, alkynyl, and aryl moieties substituted with other aliphatic, cyclic or aryl hydrocarbon groups, such as alkaryl, alkenaryl and alkynaryl. In some embodiments, "hydrocarbon" or "hydrocarbyl" comprises 1 to 30 carbon atoms.

"Hydrocarbylene" refers to a divalent group formed by removing two hydrogen atoms from a hydrocarbon, the free valencies of which are not engaged in a double bond, e.g. arylene, alkylene, alkenylene, alkynylene, aralkylene or alkarylene.

"Substituted" as used herein to describe a compound or chemical moiety refers to that at least one hydrogen atom of that compound or chemical moiety is replaced with a second chemical moiety. Non-limiting examples of substituents are those found in the exemplary compounds and embodiments disclosed herein, as well as halogen; alkyl; heteroalkyl; alkenyl; alkynyl; aryl, heteroaryl, hydroxy; alkoxyl; amino; nitro; thiol; thioether; imine; cyano; amido; phosphonato; phosphine; carboxyl; thiocarbonyl; sulfonyl; sulfonamide; ketone; aldehyde; ester; oxo; haloalkyl (e.g., trifluoromethyl); carbocyclic cycloalkyl, which can be monocyclic or fused or non-fused polycyclic (e.g., cyclopropyl, cyclobutyl, cyclopentyl or cyclohexyl) or a heterocycloalkyl, which can be monocyclic or fused or non-fused polycyclic (e.g., pyrrolidinyl, piperidinyl, piperazinyl, morpholinyl or thiazinyl); carbocyclic or heterocyclic, monocyclic or fused or non-fused polycyclic aryl (e.g., phenyl, naphthyl, pyrrolyl, indolyl, furanyl, thiophenyl, imidazolyl, oxazolyl, isoxazolyl, thiazolyl, triazolyl, tetrazolyl, pyrazolyl, pyridinyl, quinolinyl, isoquinolinyl, acridinyl, pyrazinyl, pyridazinyl, pyrimidinyl, benzimidazolyl, benzothiophenyl or benzofuranyl); amino (primary, secondary or tertiary); o-lower alkyl; o-aryl, aryl; aryl-lower alkyl; —CO$_2$CH$_3$; —CONH$_2$; —OCH$_2$CONH$_2$; —NH$_2$; —SO$_2$NH$_2$; —OCHF$_2$; —CF$_3$; —OCF$_3$; —NH(alkyl); —N(alkyl)$_2$; —NH(aryl); —N(alkyl) (aryl); —N(aryl)$_2$; —CHO; —CO(alkyl); —CO(aryl); —CO$_2$(alkyl); and —CO$_2$(aryl); and such moieties can also be optionally substituted by a fused-ring structure or bridge, for example —OCH$_2$O—. These substituents can optionally be further substituted with a substituent selected from such groups. All chemical groups disclosed herein can be substituted, unless it is specified otherwise. For example, "substituted" alkyl, alkenyl, alkynyl, aryl, hydrocarbyl or heterocyclo moieties described herein are moieties which are substituted with a hydrocarbyl moiety, a substituted hydrocarbyl moiety, a heteroatom, or a heterocyclo. Further, substituents may include moieties in which a carbon atom is substituted with a heteroatom such as nitrogen, oxygen, silicon, phosphorus, boron, sulfur, or a halogen atom. These substituents may include halogen, heterocyclo, alkoxy, alkenoxy, alkynoxy, aryloxy, hydroxy, protected hydroxy, keto, acyl, acyloxy, nitro, amino, amido, cyano, thiol, ketals, acetals, esters and ethers.

"Fluorophore" refers to a part of a molecule that causes a molecule to be fluorescent. In general, it is a functional group that can absorb radiation of a specific wavelength and re-emit radiation at a different specific wavelength. The intensity and wavelength of the emitted radiation generally depend on both the fluorophore and the chemical environment of the fluorophore.

"Fluorescent label" refers to a fluorescent molecule, whose fluorescence always keeps in "on" state, that to say, which always emits fluorescence, no matter before or after reacting with the target.

"Fluorogenic probe" refers to a latent fluorescent molecule, whose fluorescence stays in "off" state before reacting with the target and may switch to "on" state after reacting with the target.

"Hydroxy activating group" refers to a labile chemical moiety which is known in the art to activate a hydroxyl group during an activation reaction such as in a substitution reaction. For example, the hydroxy group —OH can be activated to form —OB by substituting the hydrogen with the B group. In some embodiments, B is methanesulfonyl (mesyl), p-toluenesulfonyl (tosyl), trifluoromethanesulfonyl (triflyl), nonafluorobutanesulfonyl (nonflyl) or 3-nitrobenzenesulfonyl. Some non-limiting examples of hydroxyl activating group include methanesulfonate (mesylate), p-toluenesulfonate (tosylate), trifluoromethanesulfonate (triflate), nonafluorobutanesulfonate (—OSO$_2$CF$_2$CF$_2$CF$_2$CF$_3$, nonflate), p-nitrobenzoate, phosphonate and the like.

"Hydroxy protecting group" refers to a labile chemical moiety which is known in the art to protect a hydroxy group against undesired reactions during synthetic processes. The hydroxy protecting group may be selectively removed when there is no need for its protection. Some suitable hydroxy protecting groups are described in P. G. M. Wuts and T. H. Greene, "*Greene's Protective Groups in Organic Synthesis,*" 4th edition, Wiley-Interscience, New York (2006), which is incorporated herein by reference. Some non-limited examples of hydroxy protecting groups include benzyloxycarbonyl, 4-nitrobenzyloxycarbonyl, 4-bromobenzyloxycarbonyl, 4-methoxybenzyloxycarbonyl, methoxycarbonyl, tert-butoxycarbonyl, isopropoxycarbonyl, diphenylmethoxycarbonyl, 2,2,2-trichloroethoxycarbonyl, 2-(trimethylsilyl)ethoxycarbonyl, 2-furfuryloxycarbonyl, allyloxycarbonyl, acetyl, formyl, chloroacetyl, trifluoroacetyl, methoxyacetyl, phenoxyacetyl, benzoyl, methyl, t-butyl, 2,2, 2-trichloroethyl, 2-trimethylsilyl ethyl, 1,1-dimethyl-2-propenyl, 3-methyl-3-butenyl, allyl, benzyl, p-methoxybenzyl-diphenylmethyl, triphenylmethyl (trityl), tetrahydrofuryl, methoxymethyl, methylthiomethyl, benzyloxymethyl, 2,2,2-triehloroethoxymethyl, 2-(trimethylsilyl)ethoxymethyl, methanesulfonyl, p-toluenesulfonyl, trimethylsilyl, triethylsilyl, triisopropylsilyl, and the like. In some embodiments, the hydroxy protecting group is acetyl, benzoyl, or trimethylsilyl.

"Reacting", "adding" or the like refers to contacting one reactant, reagent, solvent, catalyst, reactive group or the like with another reactant, reagent, solvent, catalyst, reactive group or the like. Reactants, reagents, solvents, catalysts, reactive group or the like can be added individually, simultaneously or separately and can be added in any order. They can be added in the presence or absence of heat and can optionally be added under an inert atmosphere. In some embodiments, "reacting" refers to in situ formation or intra-molecular reaction where the reactive groups are in the same molecule.

"High-throughput method" refers to a method that can autonomously process or evaluate a large number of samples. In some embodiments, informatics systems can be used and implemented in the high-throughput method. The informatics systems can provide the software control of the physical devices used in the high-throughput method, as well as organize and store electronic data generated by the high-throughput method "Substantially react" refers to that at least a reactant of a reaction is consumed by an amount of more than about 75% by mole, by more than about 80% by mole, by more than about 85% by mole, or by more than about 90% by mole. In some embodiments, "substantially react" refers to that the reactant is consumed by more than about 95% by mole. In other embodiments, "substantially react" refers to that the reactant is consumed by more than about 97% by mole. In further embodiments, "substantially react" refers to that the reactant is consumed by more than about 99% by mole.

DETAILED DESCRIPTION

Provided herein are fluorophore compounds or rhodol fluorophores that can be used as fluorescent labels and/or fluorogenic probes for tracking, measuring, detecting or screening biological species. In some embodiments, the fluorophore compounds or rhodol fluorophores have formula (III) or (VI) as shown in Schemes 1 and 2 below.

The fluorophore compounds of formulae (III) and (VI) can be prepared by any synthetic method known to persons skilled in the art. In some embodiments, the fluorophores of formulae (III) and (VI) are prepared according to Schemes 1 and 2 respectively below.

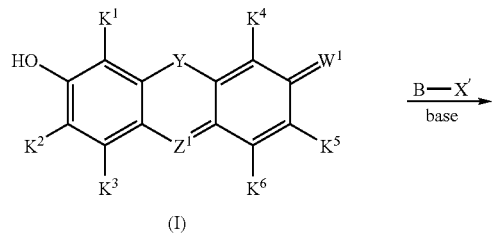

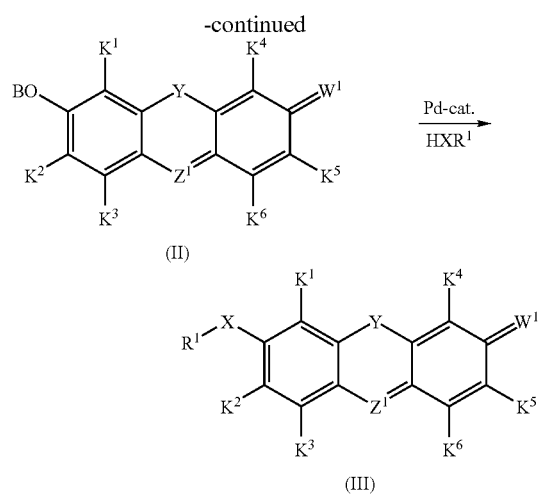

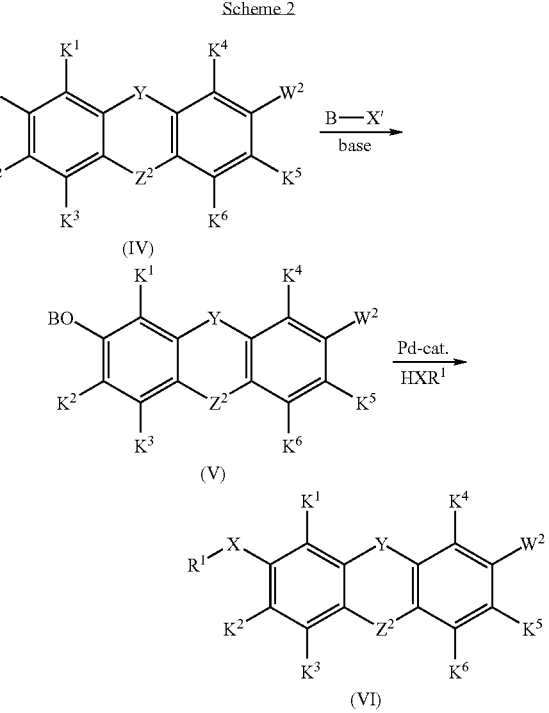

wherein OB is a hydroxy activating group;
each of $K^1$, $K^2$, $K^3$, $K^4$, $K^5$ and $K^6$ is independently a substituent;
$W^1$ is O or S;
$W^2$ is O-A, S-A or $NR^3R^4$;
X is $NR^2$, O or S;
Y is O, S, Se, $NR^5$ or $CR^6R^7$;
$Z^1$ is $CR^8$ or N;
$Z^2$ is $CR^9R^{10}$ or $NR^{11}$;
A is H, alkyl, alkenyl, alkynyl, alkoxyalkyl, heteroalkyl, cycloalkyl, cycloalkenyl, cycloalkynyl, heterocyclyl, aminoalkyl, aryl, alkaryl, arylalkyl, carboxyalkyl, alkoxycarbonyl, acyl, aminocarbonyl or a hydroxy protecting group;
each of $R^1$, $R^2$, $R^3$, $R^4$, $R^5$, $R^6$, $R^7$, $R^9$, $R^{10}$ and $R^{11}$ is independently H, alkyl, alkenyl, alkynyl, alkoxyalkyl, heteroalkyl, cycloalkyl, cycloalkenyl, cycloalkynyl, heterocyclyl, aminoalkyl, aryl, alkaryl, arylalkyl, alkyloxy, carboxyalkyl, alkylamido, alkoxyamido, sulfonylaryl, acyl or a reactive functional group, or $CR^9R^{10}$ is a substituted 2-carboxyphenyl-C group having formula (VII) or (VIIa):

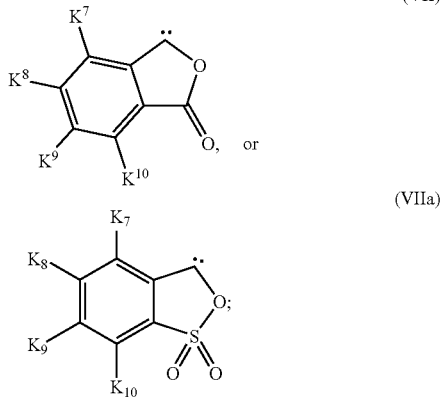

$R^8$ is H, alkyl, alkenyl, alkynyl, alkoxyalkyl, heteroalkyl, cycloalkyl, cycloalkenyl, cycloalkynyl, heterocyclyl, aminoalkyl, aryl, alkaryl, arylalkyl, alkyloxy, carboxyalkyl, alkylamido, alkoxyamido, sulfonylaryl, acyl or a reactive functional group, or has formula (VIIb) or (VIIc):

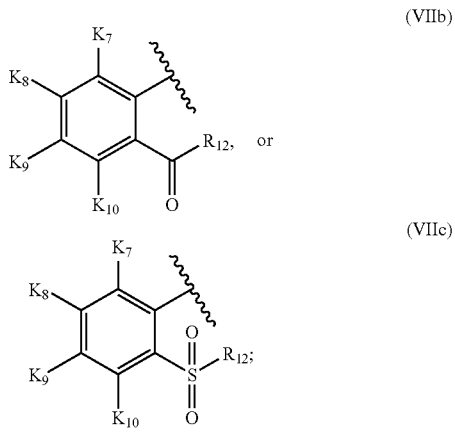

wherein each of $K^7$, $K^8$, $K^9$ and $K^{10}$ is independently H, halo, alkyl, halogenated alkyl, heteroalkyl, alkenyl, alkynyl, aryl, aralkyl, alkaryl, heterocyclyl, cycloalkyl, cycloalkenyl, cycloalkynyl, hydroxyalkyl, aminoalkyl, amino, alkylamino, arylamino, dialkylamino, alkylarylamino, diarylamino, acylamino, hydroxy, thio, thioalkyl, alkoxy, alkylthio, alkoxyalkyl, aryloxy, arylalkoxy, acyloxy, cyano, nitro, sulfhydryl, carbamoyl, trifluoromethyl, phenoxy, benzyloxy, sulfonyl, phosphonyl, sulfonate ester, phosphate ester, —C(=O)—$P^1$ or —C(=O)-Q-$P^2$, wherein each of $P^1$ and $P^2$ is independently hydrogen, halo, alkoxy, hydroxy, thio, alkyl, alkenyl, alkynyl, cycloalkyl, cycloalkenyl, cycloalkynyl, aryl, alkaryl, arylalkyl, carbamate, amino, alkylamino, arylamino, dialkylamino, alkylarylamino, diarylamino, alkylthio, heteroalkyl, or heterocyclyl having from 3 to 7 ring atoms; and Q is alkylene, alkenylene, alkynylene, arylene, aralkylene or alkarylene.

In some embodiments, $K^7$ and $K^8$ together or $K^8$ and $K^9$ together or $K^9$ and $K^{10}$ together form a part of a 5-, 6-, or 7-membered cycloalkyl, cycloalkenyl, cycloalkynyl, aryl, heteroalkyl or heteroaryl ring. In other embodiments, at least one of $K^7$, $K^8$, $K^9$ and $K^{10}$ is an electron-withdrawing group, such as halo and trifluoromethyl. In further embodiments, at least one of $K^7$, $K^8$, $K^9$ and $K^{10}$ is F or Cl. In some embodiments, $Z^2$ has formula (VII).

Each of Scheme 1 and Scheme 2 involves two steps: activation of phenol, preferred with triflate (trifluoromethanesulfonate), and subsequent cross coupling with amines. The preferred triflate may be obtained from the reaction of phenol with trifluoromethanesulfonyl-donating reagent, like trifluoromethanesulfonic anhydride, trifluoromethanesulfonyl chloride or N-phenyl-bis(trifluoromethanesulfonimide), in the presence of a base. The typical procedure and skills of choosing catalyst system for subsequent amination reaction could be found in, for example, a review entitled *Palladium-Catalyzed Amination of Aryl Halides and Related Reactions* by Hartwig, J. F. in *Handbook of Organopalladium Chemistry for Organic Synthesis*, Edited by Negishi, E., John Wiley & Sons, Inc. (2002); or a book entitled *Metal-catalyzed Cross-coupling Reactions* edited by Diederich and Stang, Wiley-VCH: Weinheim, Germany (1997), all of which are incorporated herein by reference. The amination reaction of tosylate and nonflate could also be found in Hamann et al., *J. Am Chem. Soc.* 1998, 120, 7369-7370; Huang et al., *J. Am Chem. Soc.* 2003, 125, 6653-6655; Gao et al., *J. Org. Chem.* 2008, 73, 1624-1627; Anderson et al., *J. Org. Chem.* 2003, 68, 9563-9573; and Zhang et al., *J. Fluo. Chem.* 2006, 127, 588-591, all of which are incorporated herein by reference.

B—X' is a hydroxy activating agent that reacts with —OH to form a —OB group and HX'. In some embodiments, the B—X' is mesyl halide, triflyl halide, tosyl halide, nonflyl halide, mesyl anhydride, triflyl anhydride, tosyl anhydride, nonflyl anhydride or a combination thereof. The —OB group can be any hydroxy activating group that undergoes cross coupling reaction with a nucleophile having formula $HXR^1$ in the presence of a palladium catalyst to form an —$XR^1$ group and HOB. In some embodiments, X' is a halide and B is a sulfonyl, carboxyl or phosphonyl. In other embodiments, B is mesyl, triflyl, tosyl or nonflyl. In other embodiments, X is N or O. In further embodiments, Y is O, S or $NR^5$. In still further embodiments, Y is O.

Each of $K^1$, $K^2$, $K^3$, $K^4$, $K$ and $K^6$ can be any substituent that does not affect the fluorescence properties of formula (III) or (VI). In some embodiments, each of $K^1$, $K^2$, $K^3$, $K^4$, $K^5$ and $K^6$ is independently hydrogen, halo, alkyl, halogenated alkyl, heteroalkyl, alkenyl, alkynyl, aryl, aralkyl, alkaryl, heterocyclyl, cycloalkyl, cycloalkenyl, cycloalkynyl, hydroxyalkyl, aminoalkyl, amino, alkylamino, arylamino, dialkylamino, alkylarylamino, diarylamino, acylamino, hydroxy, thio, thioalkyl, alkoxy, alkylthio, alkoxyalkyl, aryloxy, arylalkoxy, acyloxy, cyano, nitro, sulfhydryl, carbamoyl, trifluoromethyl, phenoxy, benzyloxy, sulfonyl, phosphonyl, sulfonate ester, phosphate ester, —C(=O)—$P^1$ or —C(=O)-Q-$P^2$, wherein each of $P^1$ and $P^2$ is independently hydrogen, halo, alkoxy, hydroxy, thio, alkyl, alkenyl, alkynyl, cycloalkyl, cycloalkenyl, cycloalkynyl, aryl, alkaryl, arylalkyl, carbamate, amino, alkylamino, arylamino, dialkylamino, alkylarylamino, diarylamino, alkylthio, heteroalkyl, or heterocyclyl having from 3 to 7 ring atoms; and Q is alkylene, alkenylene, alkynylene, arylene, aralkylene or alkarylene. In some embodiments, $K^2$ and $K^3$ together or $K^5$ and $K^6$ together form a part of a 5-, 6-, or 7-membered cycloalkyl, cycloalkenyl, cycloalkynyl, aryl, heteroalkyl or heteroaryl ring. In other embodiments, at least one of $K^1$, $K^2$, $K^3$, $K^4$, $K^5$ and $K^6$ is an electron-withdrawing group, such as halo and trifluoromethyl. In further embodiments, at least one of $K^1$, $K^2$, $K^3$, $K^4$, $K^5$ and $K^6$ is F or Cl.

Any catalyst that can promote the cross coupling reactions as depicted in Scheme 1 and Scheme 2 can be used herein. In some embodiments, the catalyst for the cross coupling reactions disclosed herein comprises a bulky phosphine ligand and palladium. Such catalytic reactions, phosphine ligands and reaction conditions can be found in, for example, Hartwig, J. F., "Palladium-Catalyzed Amination of Aryl Halides and Related Reactions" in Handbook of Organopalladium Chemistry for Organic Synthesis, edited by Negishi, E., John Wiley & Sons, Inc. 2002, which is incorporated herein by reference. It should be recognized that the palladium and phosphine ligand system described herein is not limited to be the only available one for this kind of reaction. Some other catalytic systems are also possible.

In some embodiments, the catalyst for the cross coupling reactions disclosed herein comprises a ligand and a palladium source. Some non-limiting examples of suitable palladium source include palladium acetate, tris(dibenzylideneacetone) dipalladium, palladium chloride and combinations thereof.

In certain embodiments, the ligand is a phosphine ligand or a carbene ligand. Some non-limiting examples of suitable phosphine ligand include rac-2,2'-bis(diphenylphosphino)-1, 1'-binaphthalene (BINAP), 1,1'-bis(diphenylphosphino)ferrocene (dppf), 2-(dicyclohexylphosphino)biphenyl, tricyclohexylphosphine, triphenylphosphine, tri-t-butylphosphine, 9,9-dimethyl-4,5-bis(diphenylphosphino)xanthene (Xantphos), 2-(di-t-butylphosphino)biphenyl, rac-2-(di-t-butylphosphino)-1,1'-binaphthyl and combinations thereof.

In some embodiments, the ligand is a carbene ligand. Some non-limiting examples of suitable palladium-carbene complex include (N-heterocyclic carbene)Pd(allyl)Cl complexes as disclosed in Navarro et al., J. Org. Chem. 2004, 69, 3173-3180, which is incorporated herein by reference.

In certain embodiments, the fluorophore of Formula (VI) disclosed herein is a rhodol fluorophore having formula (VIII):

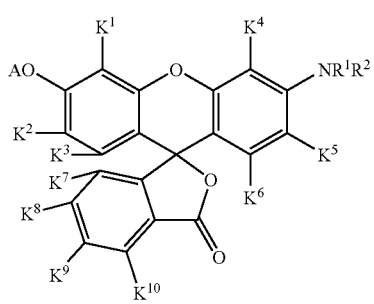

(VIII)

where X of formula (VI) is $NR^2$; $W^2$ is O-A; $Z^2$ has formula (VII) and $R^1$, $R^2$, $K^1$, $K^2$, $K^3$, $K^4$, $K^5$, $K^6$, $K^7$, $K^8$, $K^9$, $K^{10}$ and A are as disclosed herein.

In some embodiments, the A group of the rhodol fluorophore having formula (VIII) disclosed herein is H. In other embodiments, the fluorophore of Formula (VI) disclosed herein is a rhodol fluorophore having formula (IX):

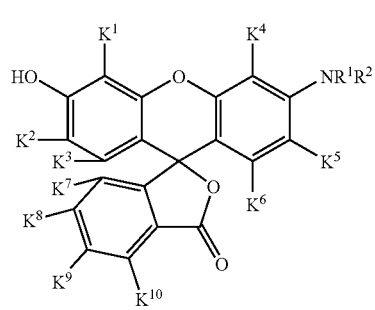

(IX)

where X of formula (VI) is $NR^2$; $W^2$ is O—A where A is H; $Z^2$ has formula (VII) and $R^1$, $R^2$, $K^1$, $K^2$, $K^3$, $K^4$, $K^5$, $K^6$, $K^7$, $K^8$, $K^9$ and $K^{10}$ are as disclosed herein.

The rhodol fluorophores of formulae (VIII) and (IX) can be prepared by any synthetic method known to persons skilled in the art. In some embodiments, the rhodol fluorophores of formulae (VIII) and (IX) can be prepared according to Scheme 3 as shown below.

Scheme 3

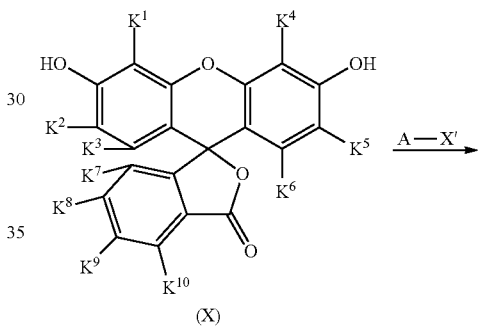

(X)

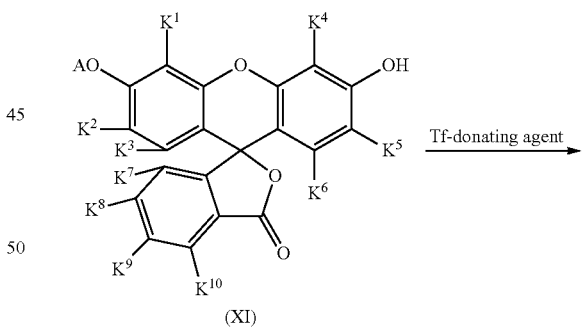

(XI)

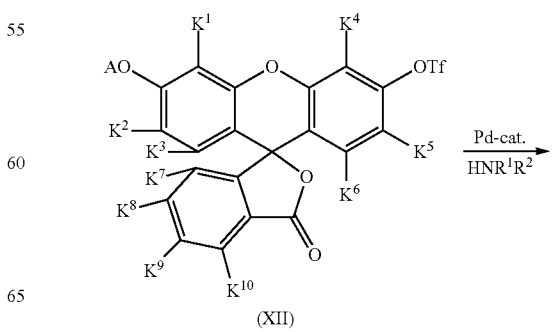

(XII)

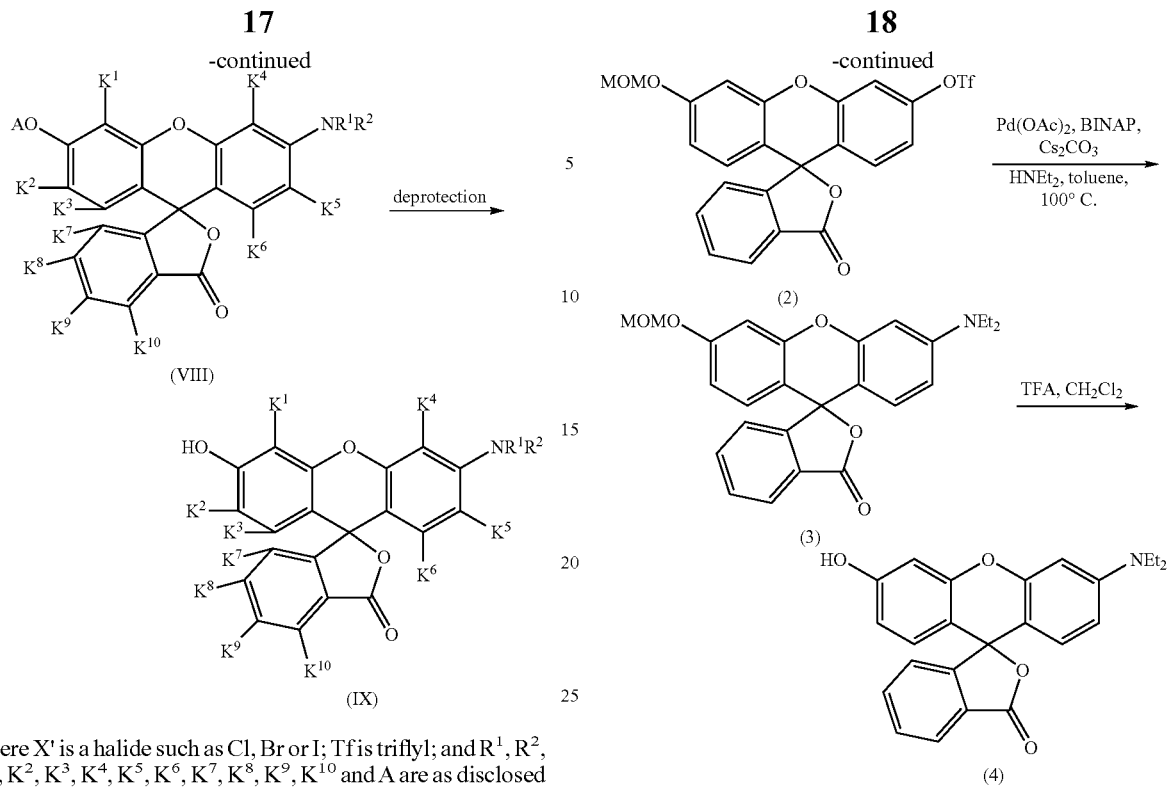

where X' is a halide such as Cl, Br or I; Tf is triflyl; and $R^1$, $R^2$, $K^1$, $K^2$, $K^3$, $K^4$, $K^5$, $K^6$, $K^7$, $K^8$, $K^9$, $K^{10}$ and A are as disclosed herein.

Rhodol fluorophores having formula (VIII) can be synthesized generally according to the procedures as shown in Scheme 3 above. First, one of the phenolic OH groups of fluorescein (X) can be mono-protected by reacting with a protecting agent, such as a halide having formula A-X', to form an O-A group. Next, the phenolic OH group of the mono-protected fluorescein (XI) can be activated by reacting with triflic acid to form a triflate group in fluorescein (XII). The triflate group of fluorescein (XII) can subsequently undergo cross-coupling reaction with an amine having formula $HNR^1R^2$ in the presence of a catalyst, such as a Pd catalyst, to form a mono-protected rhodol fluorophore (VIII). Next, the protecting group can be optionally removed under deprotection conditions to form rhodol fluorophore (IX).

In some embodiments, Compound 3, a mono-protected rhodol fluorophore of formula (VIII), and Compound 4, a rhodol fluorophore of formula (IX), can be prepared according to Scheme 4 below.

Scheme 4

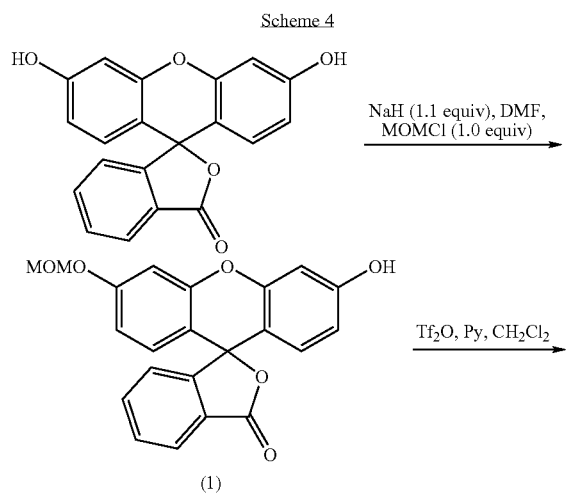

In some embodiments, the mono-protected fluorescein (XI) can be prepared by a two-step procedure. First, the fluorescein (X) can react with an excess amount of a halide having formula A-X', where A and X' are as disclosed herein, to provide a dialkylated product, one alkylation at the hydroxyl position and the other at the carboxyl acid position as an ester. Next, the ester was hydrolyzed under basic conditions to afford the mono-protected fluorescein (XI). In other embodiments, the mono-protected fluorescein (XI) having a methoxymethyl (MOM) hydroxy protecting group may be prepared in one step by reacting the fluorescein (X) with methoxymethyl chloride (MOMCl) in the presence of sodium hydride (NaH). The ratio of fluorescein to MOMCl is from about 1:1.25 to about 1.25:1, from about 1:1.1 to about 1.1:1, or about 1:1. The ratio of fluorescein to NaH is from about 1:1.25 to about 1.25:1, from about 1:1.1 to about 1.1:1, or about 1:1.1.

In certain embodiments, A may be a phenolic hydroxy protective group such as methyl, methoxymethyl, benzyloxymethyl, methoxyethoxymethyl, ethoxyethyl, allyl, propargyl, isopropyl, cyclohexyl, t-butyl, benzyl, 2,6-dimethylbenzyl, 4-methoxybenzyl, o-nitrobenzyl, 9-anthrylmethyl, 4-(dimethylamino)carbonylbenzyl, 4-picolyl, silyl, acyl, sulfonyl or the like. The above protective groups can be removed under suitable deprotection conditions to provide rhodol fluorophores having formula (IX). The hydroxy protecting groups and the protection/deprotection reaction conditions are disclosed, for example, in P. G. M. Wuts and T. H. Greene, *"Greene's Protective Groups in Organic Synthesis,"* 4th edition, Wiley-Interscience, New York (2006), which is incorporated herein by reference.

In certain embodiments, Compounds 5, 6 and 7, mono-protected rhodol fluorophores of formula (VIII), and Compound 8, a rhodol fluorophore of formula (III), can be prepared according to Scheme 5 below.

Scheme 5

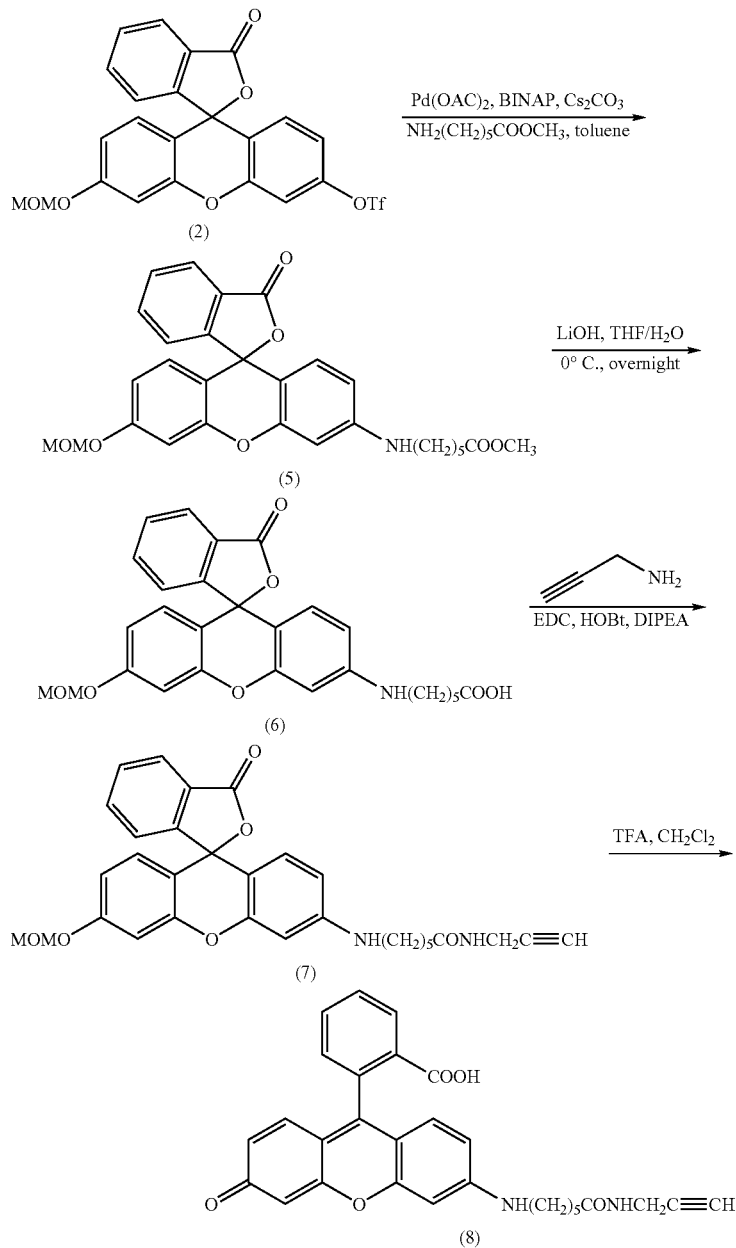

In some embodiments, A is methoxymethyl (MOM) group which may be simply removed by trifluoroacetic acid (TFA) in dichloromethane. In other embodiments, A may be alkyl, alkenyl, alkynyl, alkoxyalkyl, heteroalkyl, cycloalkyl, cycloalkenyl, cycloalkynyl, heterocyclyl, aminoalkyl, aryl, alkaryl, arylalkyl, carboxyalkyl, alkoxycarbonyl, acyl, aminocarbonyl or the like.

In some embodiments, the activating group B for the hydroxyl group may be triflic (trifluoromethanesulfonyl), tosyl or nonflic. In other embodiments, B is triflic group.

In certain embodiments, the catalyst for the cross coupling reaction may be palladium and bulky phosphine ligand system. The cross coupling reaction, palladium catalyst, suitable ligands, and cross coupling reaction conditions are disclosed in, for example, a review entitled *Palladium-Catalyzed Amination of Aryl Halides and Related Reactions* by Hartwig, J. F. in *Handbook of Organopalladium Chemistry for Organic Synthesis* (Edited by Negishi, E., John Wiley & Sons, Inc. 2002). It should be recognized that suitable catalyst and ligand system for the cross coupling reaction are not limited to the palladium and phosphine ligand system disclosed herein. Other catalytic and ligand systems known to skilled artisans can also be used.

As many different rhodol fluorophores and derivatives can be prepared through the versatile synthetic procedures disclosed herein, high throughput screening methodologies can be used in evaluating their fluorescent properties. A fluorescence plate reader with wells containing a plurality of different rhodol fluorophores disclosed herein can be loaded with known quantities of analytes and their relative fluorescence intensities may provide a quick screening process for the fluorescent properties of the rhodol fluorophores with and without the analytes.

In some embodiments, the fluorophore compound of Formula (IV) disclosed herein has formula (XIII):

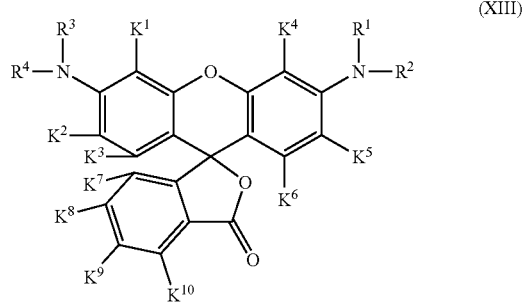

where X of formula (VI) is $NR^2$; $W^2$ is $NR^3R^4$; $Z^2$ has formula (VII) and $R^1$, $R^2$, $R^3$, $R^4$, $K^1$, $K^2$, $K^3$, $K^4$, $K^5$, $K^6$, $K^7$, $K^8$, $K^9$ and $K^{10}$ are as disclosed herein.

In certain embodiments, the fluorophore compounds of formula (XIII) can be prepared according to Scheme 6 as shown below.

where Tf is triflyl; and $R^1$, $R^2$, $R^3$, $R^4$, $K^1$, $K^2$, $K^3$, $K^4$, $K^5$, $K^6$, $K^7$, $K^8$, $K^9$ and $K^{10}$ are as disclosed herein.

In some embodiments, the fluorophore compound of Formula (IV) disclosed herein has formula (XV):

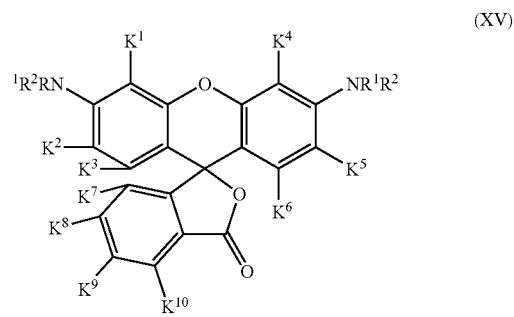

where X of formula (VI) is $NR^2$; $W^2$ is $NR^3R^4$ where $R^1$ is same as $R^3$ and $R^2$ is same as $R^4$; $Z^2$ has formula (VII) and $R^1$, $R^2$, $K^1$, $K^2$, $K^4$, $K^5$, $K^6$, $K^7$, $K^8$, $K^9$ and $K^{10}$ are as disclosed herein.

In certain embodiments, the fluorophore compound having formula (XV) can be prepared according to Scheme 7 as shown below.

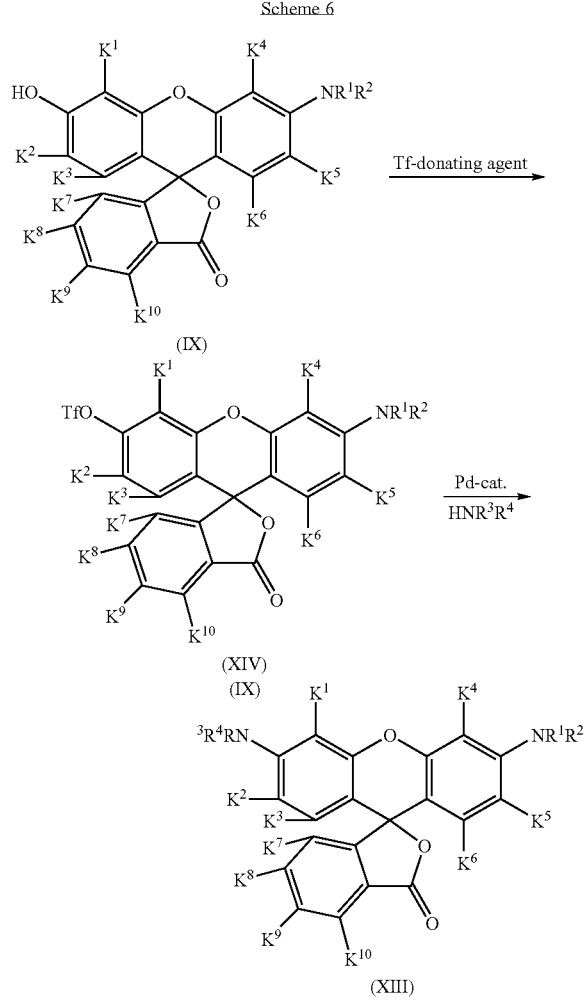

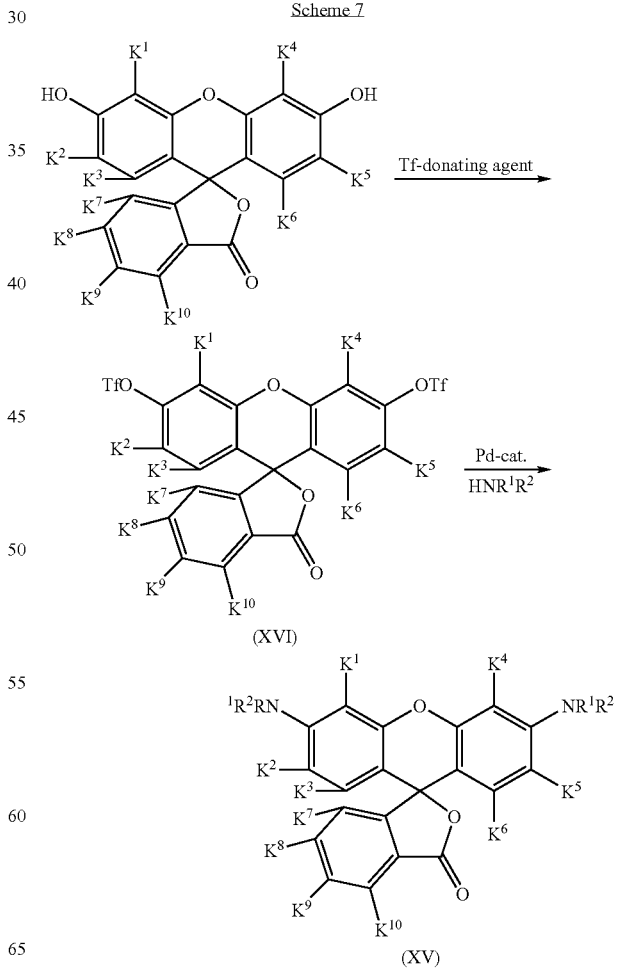

where Tf is triflyl; and $R^1$, $R^2$, $R^3$, $R^4$, $K^1$, $K^2$, $K^3$, $K^4$, $K^5$, $K^6$, $K^7$, $K^8$, $K^9$ and $K^{10}$ are as disclosed herein.

Exemplary Applications of Fluorophore Compounds Disclosed Herein

The fluorophore compounds disclosed herein can be used as fluorescent labels for biological species and/or fluorogenic probes for certain analytes. In some embodiments, one or more of the fluorophore compounds of formula (III), (VI), (VIII), (IX), (XIII) and (XIV) can be used as a fluorescent label and/or a fluorogenic probe. In other embodiments, one or more of the rhodol fluorophores such as Compounds (3), (4), (5), (6), (7) and (8) can be used as a fluorescent label and/or a fluorogenic probe. In further embodiments, the rhodol fluorophores of formula (VIII) are used as fluorescent labels and/or fluorogenic probes. In still further embodiments, the fluorescent labels or fluorogenic probes are the rhodol fluorophores of formula (VIII):

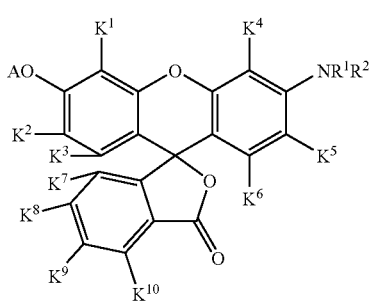

(VIII)

where X of formula (VI) is $NR^2$; $W^2$ is O-A; $Z^2$ has formula (VII) and $R^1$, $R^2$, $K^1$, $K^2$, $K^3$, $K^4$, $K^5$, $K^6$, $K^7$, $K^8$, $K^9$, $K^{10}$ and A are as disclosed herein.

1. Fluorescent Labels

In certain embodiments, the rhodol fluorophores of formula (VIII) are chemically reactive and may be used as tracers of biologically related species. In this instance, each of A, $R^1$ and $R^2$ is independently hydrogen, alkyl, alkenyl, alkynyl, alkoxyalkyl, heteroalkyl, cycloalkyl, cycloalkenyl, cycloalkynyl, heterocyclyl, aminoalkyl, aryl, alkaryl, arylalkyl, alkyloxy, carboxyalkyl, alkylamido, alkoxyamido or acyl.

As disclosed herein, rhodol fluorophores having formula (VIII) can be prepared according to the general procedures described in Schemes 4 and 5 above. As shown in Table 1 below, a library of rhodol compounds having formula (VIII), wherein each of $K^1$, $K^2$, $K^3$, $K^4$, $K^5$, $K^6$, $K^7$, $K^8$, $K^9$ and $K^{10}$ is H, have been prepared according to the general procedures described in Schemes 4 and 5 above. The A, $R^1$ and $R^2$ groups for each rhodol fluorophore are also shown in Table 1. In general, the data in Table 1 show that some of the rhodol compounds are strongly fluorescent.

TABLE 1

| Compounds | | | Abs Max[a] (nm) | $\epsilon_{max}$[a] (cm$^{-1}$M$^{-1}$) | Em Max[a] (nm) | QY[a,b] | Purity[c] (%) |
|---|---|---|---|---|---|---|---|
| A | $R_1$ | $R_2$ | | | | | |
| H | H | H | 493 | ~70,000 | 516 | 0.98 | 93 |
| H | CH$_2$CH$_2$CH$_2$CH$_2$CH$_2$ | | 523 | 62,500 | 555 | 0.03 | 100 |
| H | Me | Me | 518 | 64,000 | 544 | 0.20 | 100 |
| H | Et | Et | 522 | 47,000 | 549 | 0.08 | 98 |
| H | n-Bu | n-Bu | 525 | 63,000 | 553 | 0.12 | 99 |
| H | H | n-Pr | 507 | 61,000 | 531 | 0.94 | 98 |
| H | H | n-Bu | 508 | 60,000 | 533 | 0.90 | 95 |
| H | H | Bn | 503 | 71,000 | 529 | 0.95 | 100 |
| H | H | Ph | 513 | 55,000 | N.D.[d] | N.D.[d] | 100 |
| H | H | COPh | 462/490 | — | 525 | 0.16 | 100 |
| H | H | COCHCH$_2$ | 462/490 | — | 524 | 0.19 | 100 |
| Me | H | H | 477 | — | 516 | 0.85 | 100 |
| MOM | H | n-Pr | 494 | — | 532 | 0.35 | — |
| MOM | H | COPh | 293 | — | N.D.[d] | N.D.[d] | — |

Note:
[a]Sample was in 50 mM aqueous phosphate buffer at pH about 8.0.
[b]Determined using rhodamine 6G (QY = 0.76 in water) as a reference.
[c]Determined by HPLC.
[d]No fluorescence detected.

In some embodiments, at least one of A, $R^1$ and $R^2$ is a chemically reactive functional group that can couple with or react with or bond to a corresponding reactive site in target molecules. Some non-limiting examples of the chemically reactive functional compounds of the rhodol fluorophores and the reactive sites of the target molecules are listed in Table 2. The tabulation is not meant to be inclusive of chemical reactivity since with the appropriate choice of solvent, co-solvent, stoichiometric ratio, temperature, pressure, reaction time, pH, catalyst and the like, other functional groups can be made to react with the reactive sites disclosed herein whereas the functional groups disclosed herein can be made to react with other reactive sites. Some non-limiting examples of suitable reactive functional groups include groups that are derived from acrylamide, acyl azide, acyl halide, nitrile, aldehyde, ketone, alkyl halide, alkyl sulfonate, anhydride, aryl halide, alkyne, alcohol, amine, carboxylic acid, carbodiimide, diazoalkane, epoxide, haloacetamide, hydroxylamine, hydrazine, imido ester, isothiocyanate, maleimide, sulfonate ester or sulfonyl halide. In some embodiments, the reactive functional groups are derived from acrylamide, acyl azide, acyl halide, nitrile, aldehyde, ketone, alkyl halide, alkyl sulfonate, anhydride, aryl halide, alkyne, alcohol, amine, carboxylic acid, carbodiimide, diazoalkane, epoxide, haloacetamide, hydroxylamine, hydrazine, imido ester, isothiocyanate, maleimide, sulfonate ester or sulfonyl halide by removing from them a hydrogen or a monovalent atom or group such as OH or halide.

TABLE 2

Some Reactive Functional Groups Used in Fluorescent Labeling

| Reactive Functional groups | Reactive Sites | Resulting Linkage |
|---|---|---|
| activated esters (succinimide esters) | amines/anilines | amides |
| acrylamides | thiols | thioethers |
| acyl azides | amines/anilines | amides |
| acyl halides | amines/anilines | amides |
| acyl halides | alcohols/phenols | esters |
| acyl nitriles | alcohols/phenols | esters |
| acyl nitriles | amines/anilines | amides |
| aldehydes | amines/anilines | imines |
| aldehydes or ketones | hydrazines | hydrazones |
| aldehydes or ketones | hydroxylamines | oximes |
| alkyl halides | amines/anilines | alkyl amines |
| alkyl halides | carboxylic acids | esters |
| alkyl halides | thiols | thioethers |
| alkyl halides | alcohols/phenols | ethers |
| alkyl sulfonates | thiols | thioethers |
| alkyl sulfonates | carboxylic acids | esters |
| alkyl sulfonates | alcohols/phenols | ethers |
| anhydrides | alcohols/phenols | esters |
| anhydrides | amines/anilines | amides |
| aryl halides | thiols | thiophenols |
| aryl halides | amines | aryl amines |
| alkynes | azides | triazoles |
| alcohols | acid derivatives | esters |
| amines | carboxylic acids | amides |
| amines | halides | alkyl amines |
| amines | aldehydes/ketones | imines |
| carboxylic acids | amines/anilines | amides |
| carboxylic acids | alcohols | esters |
| carboxylic acids | hydrazines | hydrazides |
| carbodiimides | carboxylic acids | N-acylureas or anhydrides |
| diazoalkanes | carboxylic acids | esters |
| epoxides | thiols | thioesters |
| haloacetamides | thiols | thioethers |
| hydroxylamines | aldehydes/ketones | oximes |
| hydrazines | aldehydes/ketones | hydrazones |
| imido esters | amines/anilines | amidines |

TABLE 2-continued

Some Reactive Functional Groups Used in Fluorescent Labeling

| Reactive Functional groups | Reactive Sites | Resulting Linkage |
|---|---|---|
| isothiocyanates | amines/anilines | thioureas |
| isothiocyanates | alcohols/phenols | isourethanes |
| maleimides | thiols | thioethers |
| maleimides | amines | amines |
| sulfonate esters | amines/anilines | alkyl amines |
| sulfonate esters | thiols | thioesters |
| sulfonate esters | carboxylic acids | esters |
| sulfonate esters | alcohols | ethers |
| sulfonyl halides | amines/anilines | sulfonamides |
| sulfonyl halides | phenols/alcohols | sulfonate esters |

In some embodiments, each of A and $R^1$ of the rhodol compounds having formula (VIII) is hydrogen; and $R^2$ is a chemically reactive functional group disclosed herein. In further embodiments, each of $K^1, K^2, K^3, K^4, K^5, K^6, K^7, K^8, K^9$ and $K^{10}$ is H. Such rhodol compounds may show very strong fluorescence with a quantum yield of about 0.9. Therefore, they may be suitable to be used as fluorescent labels.

2. Fluorogenic Substrate for Enzyme

The rhodol compounds having formula (VIII) can also be used as fluorogenic probes for detection of enzyme activities. In this case, the rhodol fluorogenic probes disclosed herein are enzyme substrate analogues, and their fluorescences might be finely switched on after enzymatic reactions.

In certain embodiments, the rhodol fluorogenic probes having formula (VIII) may be used to detect activities of certain aminopeptidases. In some embodiments, each of $R^1$ and $R^2$ is independently hydrogen and a C-terminal residue of a corresponding peptide; A is H, alkyl, alkenyl, alkynyl, alkoxyalkyl, heteroalkyl, cycloalkyl, cycloalkenyl, cycloalkynyl, heterocyclyl, aminoalkyl, aryl, alkaryl, arylalkyl, carboxyalkyl, alkoxycarbonyl, acyl, aminocarbonyl or a hydroxy protecting group. In other embodiments, the rhodol fluorogenic probes or substrates for aminopeptidase are trypsin substrate (VII), b-glucosidase substrate (VIII), caspase substrate (IX), and esterase substrate (X) as shown below:

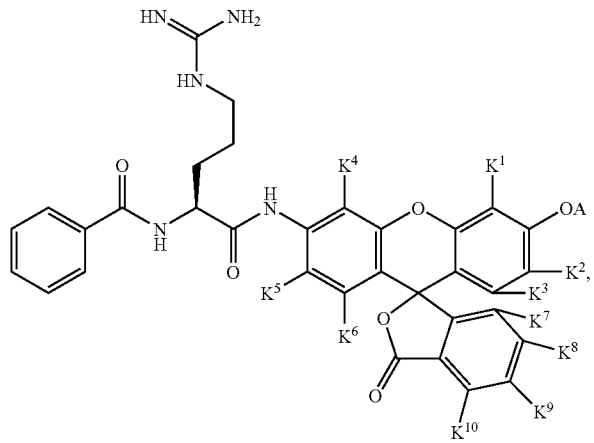

(XVII)

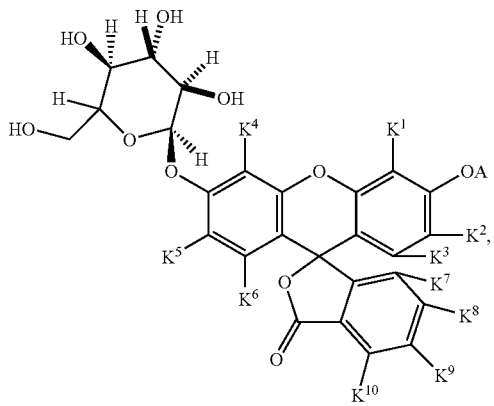

(XVIII)

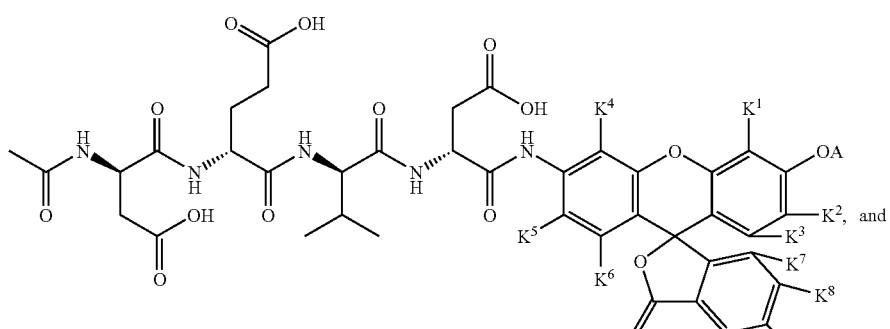

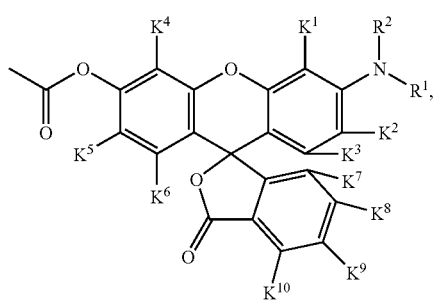

where A, R$^1$, R$^2$, K$^1$, K$^2$, K$^3$, K$^4$, K$^5$, K$^6$, K$^7$, K$^8$, K$^9$ and K$^{10}$ are as disclosed herein. In some embodiments, each of K$^1$, K$^2$, K$^3$, K$^4$, K$^5$, K$^6$, K$^7$, K$^8$, K$^9$ and K$^{10}$ is H.

Also it is to be recognized that the exemplary applications described herein are only meant to show the application potential of rhodol fluorophores disclosed herein, and not to exhaust all the possible applications for the rhodol fluorophores disclosed herein, such as the library of rhodol compounds shown in Table 1. Other potential applications are also considered to fall within the scope of this disclosure.

EXAMPLES

The following Examples 1-9 are detailed descriptions of the methods of making and using the fluorogenic probes disclosed herein, such as those represented by formulae (III), (VI), (VIII), (IX), (XIII) and (XIV). The detailed disclosure falls within the scope of, and serves to exemplify, the synthetic procedures disclosed herein, such as Schemes 1-7. These examples are presented for illustrative purposes only and are not intended to limit the scope of this disclosure. It is also to be understood that certain changes and modifications which are apparent to one skilled in the art are included in the purview and intent of this disclosure.

Preparation of Example 1

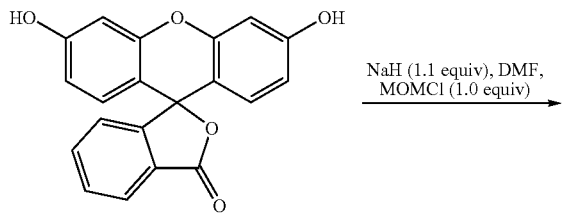

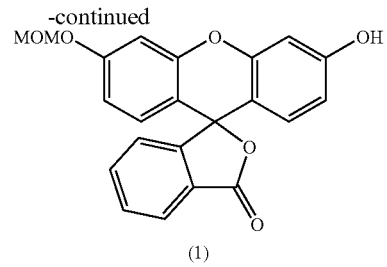

To a solution of fluorescein (3.3 g, 10 mmol) in 50 mL of anhydrous dimethylforamide (DMF) was added sodium hydride (NaH) (437 mg, 11 mmol, and 60% dispersion in mineral oil) at 0° C. After being stirred at 0° C. for half an hour, an amount of methoxymethyl chloride (MOMCl) (0.76 mL, 10 mmol) was added to the solution. The resulting mixture was stirred at room temperature overnight and then quenched with water. After that, 1N of hydrochloride (HCl) was added to the mixture to acidify the solution to pH 2. Ethyl acetate was then added. The organic layer was separated and washed with brine, dried over anhydrous sodium sulfate and evaporated in vacuo. The residue was purified by silica gel column chromatography to give Example 1 (3.2 g, 85% yield). Example 1 was characterized by the following spectroscopic data: $^1$H NMR (400 MHz, CDCl$_3$) δ 8.01 (d, J=7.6 Hz, 1H), 7.66-7.59 (m, 2H), 7.14 (d, J=7.6 Hz, 1H), 6.92 (d, J=1.7 Hz, 1H), 6.73 (d, J=1.9 Hz, 1H), 6.68-6.67 (m, 2H), 6.55-6.54 (m, 2H), 5.18 (s, 2H), 3.46 (s, 3H); $^{13}$C NMR (100 MHz, CDCl$_3$) δ 170.6, 158.7, 158.6, 152.8, 152.4, 152.3, 135.3 (CH), 129.8 (CH), 129.0 (CH), 128.9 (CH), 126.5, 125.0 (CH), 124.0 (CH), 112.9 (CH), 112.6 (CH), 112.0, 110.2, 103.5 (CH), 103.1 (CH), 94.1 (CH$_2$), 85.2, 56.1 (CH$_3$); LRMS (EI) m/z (%) 376 (M$^+$; 7), 332 (100); and HRMS (EI) for C$_{22}$H$_{16}$O$_6$: the calculated molecular weight was 376.0947, and the found molecular weight was 376.0949.

Preparation of Example 2

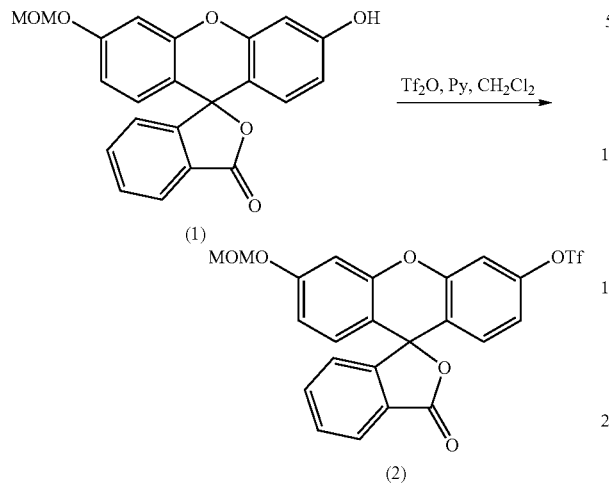

To a solution of Example 1 (3.2 g, 8.5 mmol) and pyridine (2.74 mL, 34 mmol) in dry dichloromethane ($CH_2Cl_2$) under argon (Ar) gas was added trifluoromethanesulfonic anhydride (2.86 mL, 17 mmol) dropwise at 0° C. The resulting solution was stirred at room temperature for two hours and then quenched with water. Dichloromethane ($CH_2Cl_2$) was added to the mixture. The organic layer was separated, washed with 1N of hydrochloride (HCl) followed by water and brine. The organic layer was then dried over anhydrous sodium sulfate and concentrated. The residue was purified by silica gel column chromatography to give Example 2 (4.2 g, 98% yield). Example 2 was characterized by the following spectroscopic data: $^1$H NMR (400 MHz, $CDCl_3$) δ 8.04 (d, J=7.5 Hz, 1H), 7.72-7.65 (m, 2H), 7.27 (d, J=2.3 Hz, 1H), 7.18 (d, J=7.4 Hz, 1H), 7.01-6.93 (m, 3H), 6.77-6.73 (m, 2H), 5.19 (s, 2H), 3.46 (s, 3H); $^{13}$C NMR (100 MHz, $CDCl_3$) δ 168.7, 159.0, 152.3, 151.9, 151.5, 149.8, 135.3 (CH), 130.1 (CH), 129.9 (CH), 128.8 (CH), 126.0, 125.1 (CH), 123.7 (CH), 123.0, 120.1, 119.7, 116.9, 116.5 (CH), 113.6 (CH), 111.6, 110.3 (CH), 103.5 (CH), 94.1 ($CH_2$), 81.3, 55.9 ($CH_3$); $^{19}$F NMR (377 MHz, $CDCl_3$) δ −72.7; LRMS (EI) m/z (%) 508 (M⁻; 23), 331 (100); and HRMS (EI) for $C_{23}H_{15}F_3O_8S$: the calculated molecular weight was 508.0440, and the found molecular weight was 508.0438.

Preparation of Example 3

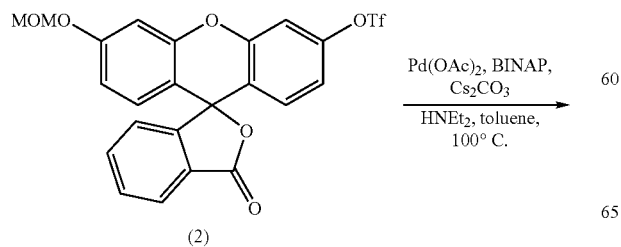

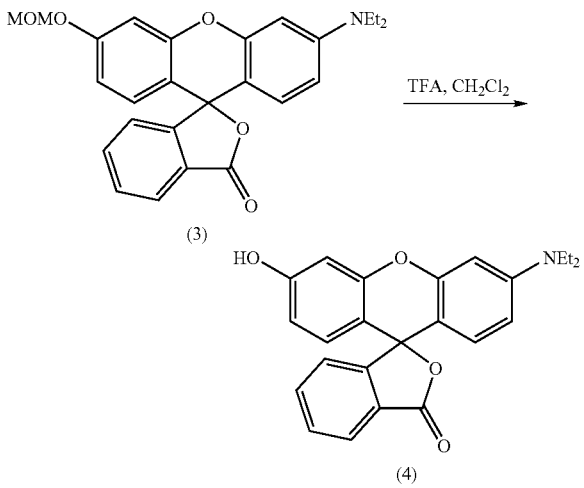

An oven-dried Schlenk tube was charged with palladium (II) acetate (1 mg, 0.5% mmol), 2,2'-bis(diphenylphosphino)-1,1'-binaphthyl (BINAP) (5 mg, 0.75% mmol) and cesium carbonate ($Cs_2CO_3$) (49 mg, 1.5 mmol), and flushed with argon (Ar) gas for 5 minutes. A solution of Example 2 (51 mg, 0.1 mmol) and N,N-diethyl amine ($Et_2NH$) (0.1 mL, 1 momol) in toluene (2 mL) was added. The resulting mixture was first stirred under argon (Ar) gas at room temperature for 30 minutes and then at 100° C. for 20 hours. The reaction mixture was allowed to cool to room temperature, diluted with dichloromethane ($CH_2Cl_2$) and filtered through a pad of Celite. The filter cake was washed three times with 5 mL of dichloromethane ($CH_2Cl_2$). The filtrate was then concentrated and the residue was purified by silica gel column chromatography to give Example 3 (26 mg, 60% yield). Example 3 was characterized by the following spectroscopic data: $^1$H NMR (400 MHz, $CDCl_3$) δ 8.00 (d, J=7.4 Hz, 1H), 7.65-7.59 (m, 2H), 7.18 (d, J=7.4 Hz, 1H), 6.94 (s, 1H), 6.67 (s, 2H), 6.56 (d, J=8.9 Hz, 1H), 6.44 (d, J=2.5 Hz, 1H), 6.35 (dd, J=8.9, 2.5 Hz, 1H), 5.19 (s, 2H), 3.47 (s, 3H), 3.35 (q, J=7.1 Hz, 4H), 1.17 (t, J=7.0 Hz, 6H); $^{13}$C NMR (100 MHz, $CDCl_3$), δ 169.6, 158.6, 153.1, 152.9, 152.7, 149.5, 134.7 (CH), 129.4 (CH), 129.1 (CH), 128.8 (CH), 127.2, 124.8 (CH), 124.0 (CH), 112.4 (CH), 108.3 (CH), 105.1, 103.5 (CH), 97.6 (CH), 94.3 ($CH_2$), 84.2, 56.1 ($CH_3$), 44.4 ($CH_2$), 12.5 ($CH_3$); LRMS (EI) m/z (%) 431 (M⁻; 21), 387 (100); and HRMS (EI) for $C_{26}H_{25}NO_5$: the calculated molecular weight was 431.1733, and the found molecular weight was 431.1739.

Preparation of Example 4

To a solution of Example 3 (26 mg, 0.06 mmol) in dry dichloromethane (CH$_2$Cl$_2$) (1 mL) was added trifluoroacetic acid (1 mL) dropwise at 0° C. The resulting solution was stirred at room temperature until the thin layer chromatography (TLC) indicated that all starting material was consumed. The mixture was then concentrated in vacuo and azeotroped with toluene three times to give Example 4 (30 mg). Analytical high performance liquid chromatography (HPLC) showed that Example 4 was pure enough for the measurement of photophysical properties. Example 4 was characterized by the following spectroscopic data: $^1$H NMR (400 MHz, CD$_3$OD) δ 8.36 (d, J=7.7 Hz, 1H), 7.85-7.78 (m, 2H), 7.40 (d, J=7.7 Hz, 1H), 7.24-7.10 (m, 4H), 7.04 (d, J=2.2 Hz, 1H), 6.95 (dd, J=8.5, 2.2 Hz, 1H), 3.69 (q, J=7.1 Hz, 4H), 1.30 (t, J=7.0 Hz, 6H); $^{13}$C NMR (100 MHz, CD$_3$OD) δ 167.4, 166.6, 161.8, 159.0, 157.4, 156.9, 133.6, 132.6, 132.0, 131.2, 131.1, 130.8, 130.3, 130.0, 117.0, 116.5, 115.6, 115.2, 102.0, 96.0, 46.1, 11.5; LRMS (EI) m/z (%) 387 (M$^+$; 35), 342 (100); and HRMS (EI) for C$_{24}$H$_{21}$NO$_4$: the calculated molecular weight was 387.1471, and the found molecular weight was 387.1472.

Preparation of Example 5

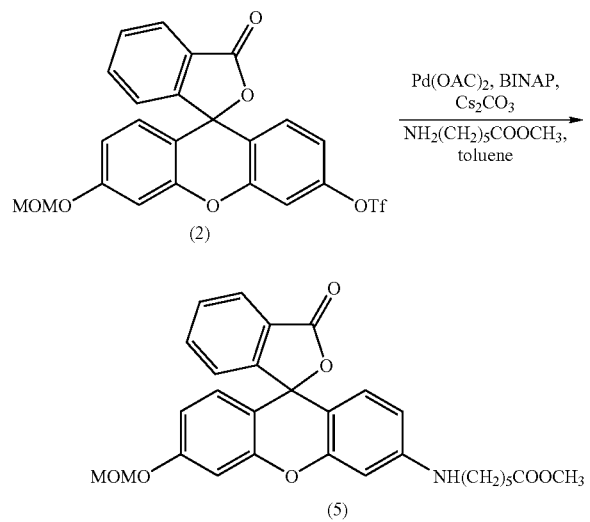

An oven-dried Schlenk tube was charged with palladium (II) acetate (Pd(OAc)$_2$) (5.6 mg, 0.025 mmol), 2,2'-bis(diphenylphosphino)-1,1'-binaphthyl (BINAP) (23 mg, 0.0375 mmol), cesium carbonate (Cs$_2$CO$_3$) (407 mg, 1.25 mmol) and methyl 6-aminohexanoate hydrochloride (109 mg, 0.6 mmol), and flushed with argon (Ar) gas for 5 minutes. Then a solution of Example 2 (254 mg, 0.5 mmol) in toluene (5 mL) was introduced. The resulting mixture was first stirred under argon (Ar) gas at room temperature for 30 minutes and then at 100° C. for 20 hours. The reaction mixture was allowed to cool to room temperature, diluted with dichloromethane (CH$_2$Cl$_2$) and filtered through a pad of Celite. The filter cake was washed three times with 15 mL of dichloromethane (CH$_2$Cl$_2$). The filtrate was then concentrated and the residue was purified by silica gel column chromatography to give Example 5 (226 mg, 90% yield). Example 5 was characterized by the following spectroscopic data: $^1$H NMR (400 MHz, CDCl$_3$) δ 8.00 (d, J=7.5 Hz, 1H), 7.64-7.58 (m, 2H), 7.16 (d, J=7.5 Hz, 1H), 6.93 (d, J=1.5 Hz, 1H), 6.68-6.67 (m, 2H), 6.51 (d, J=8.6 Hz, 1H), 6.38 (d, J=2.3 Hz, 1H), 6.26 (dd, J=8.6 Hz, 1H), 5.18 (s, 2H), 3.67 (s, 3H), 3.47 (s, 3H), 3.12 (t, J=7.0 Hz, 2H), 2.37 (t, J=7.5 Hz, 2H), 1.69-1.61 (m, 4H), 1.47-1.42 (m, 2H); $^{13}$C NMR (100 MHz, CDCl$_3$) δ 179.2, 169.7, 158.6, 153.1, 152.8, 152.5, 150.4, 134.8 (CH), 129.4 (CH), 129.0 (CH), 128.8 (CH), 127.1, 124.8 (CH), 124.0 (CH), 112.7, 112.5 (CH), 110.3 (CH), 106.8, 103.5 (CH), 97.9 (CH), 94.3 (CH$_2$), 84.5, 56.1 (CH$_3$), 51.5 (CH$_3$), 43.3 (CH$_2$), 33.8 (CH$_2$), 28.8 (CH$_2$), 26.4 (CH$_2$), 24.3 (CH$_2$); LRMS (EI) m/z 503 (M$^+$; 3), 460 (30), 129 (100); and HRMS (EI) for C$_{29}$H$_{29}$NO$_7$: the calculated molecular weight was 503.1944, and the found molecular weight was 503.1945.

Preparation of Example 6

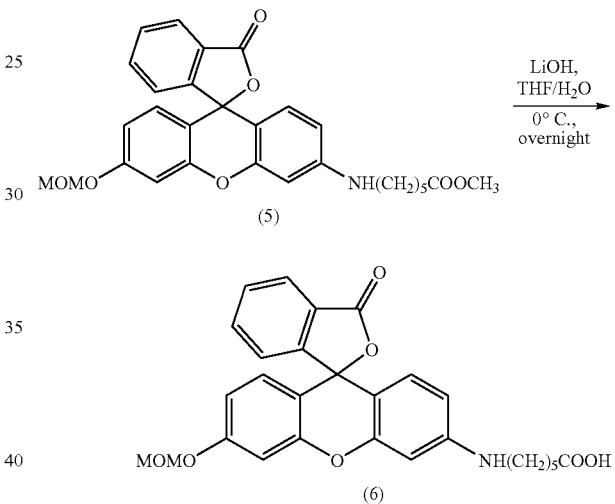

To a solution of Example 5 (226 mg, 0.45 mmol) in tetrahydrofuran (THF) (6 mL) and water (2 mL) was added lithium hydroxide monohydrate (LiOH.H$_2$O) (95 mg, 2.25 mmol) at 0° C. The reaction mixture was stirred at 0° C. until all starting material was consumed. After that, the mixture was acidified with 1 N of hydrochloride (HCl). The solution was saturated with sodium chloride (NaCl) and extracted three times with 15 mL of ethyl acetate. The combined organic layer was dried over anhydrous sodium sulfate and concentrated. The residue was purified by silica gel column chromatography to give Example 6 (187 mg, 85% yield). Example 6 was characterized by the following spectroscopic data: $^1$H NMR (400 MHz, CDCl$_3$) δ 8.00 (d, J=7.5 Hz, 1H), 7.64-7.58 (m, 2H), 7.16 (d, J=7.5 Hz, 1H), 6.93 (d, J=1.5 Hz, 1H), 6.68-6.67 (m, 2H), 6.51 (d, J=8.6 Hz, 1H), 6.38 (d, J=2.3 Hz, 1H), 6.26 (dd, J=8.6 Hz, 1H), 5.18 (s, 2H), 3.47 (s, 3H), 3.12 (t, J=7.0 Hz, 2H), 2.37 (t, J=7.5 Hz, 2H), 1.69-1.61 (m, 4H), 1.47-1.42 (m, 2H); $^{13}$C NMR (100 MHz, CDCl$_3$) δ 179.2, 169.7, 158.6, 153.1, 152.8, 152.5, 150.4, 134.8 (CH), 129.4 (CH), 129.0 (CH), 128.8 (CH), 127.1, 124.8 (CH), 124.0 (CH), 112.7, 112.5 (CH), 110.3 (CH), 106.8, 103.5 (CH), 97.9 (CH), 94.3 (CH$_2$), 84.5, 56.1 (CH$_3$), 43.3 (CH$_2$), 33.8 (CH$_2$), 28.8 (CH$_2$), 26.4 (CH$_2$), 24.3 (CH$_2$); LRMS (EI) m/z 445 (22), 129 (100); LRMS (FAB) m/z 489 (M$^-$); and HRMS (EI) for C$_{27}$H$_{26}$NO$_5$ (M$^+$-HCO$_2$): the calculated molecular weight was 444.1811, and the found molecular weight was 444.1816.

Preparation of Example 7

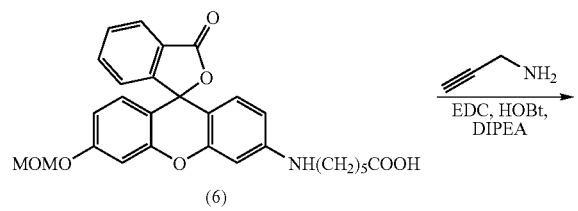

To a solution of Example 6 (187 mg, 0.38 mmol) in dichloromethane (CH$_2$Cl$_2$) were added propargylamine (53 µL, 0.76 mmol), 1-hydroxybenzotriazole (HOBt) (57 mg, 0.42 mmol), N-(3-dimethylaminopropyl)-N'-ethylcarbodiimide hydrochloride (EDC.HCl) (81 mg, 0.42 mmol) and N,N-diisopropylethylamine (73 µL, 0.42 mmol). The reaction mixture was stirred overnight and then diluted with dichloromethane (CH$_2$Cl$_2$). The organic layer was washed with saturated sodium bicarbonate (NaHCO$_3$) solution followed by 0.1 N of hydrochloride (HCl) and brine. The extract was dried over anhydrous sodium sulfate, concentrated and purified by silica gel column chromatography to give Example 7 (174 mg, 87% yield). Example 7 was characterized by the following spectroscopic data: $^1$H NMR (400 MHz, CDCl$_3$) δ 8.00 (d, J=7.5 Hz, 1H), 7.65-7.59 (m, 2H), 7.17 (d, J=7.5 Hz, 1H), 6.94 (d, J=1.5 Hz, 1H), 6.68-6.67 (m, 2H), 6.50 (d, J=8.6 Hz, 1H), 6.37 (1H), 6.26 (dd, J=8.6 Hz, 1H), 5.95 (br, 1H), 5.19 (s, 2H), 4.03-4.02 (m, 2H), 3.47 (s, 3H), 3.10 (t, J=6.8 Hz, 2H), 2.21-2.17 (m, 3H), 1.70-1.57 (m, 4H), 1.43-1.36 (m, 2H); $^{13}$C NMR (100 MHz, CDCl$_3$) δ 172.5, 169.7, 158.6, 153.1, 152.8, 152.5, 150.4, 134.8 (CH), 129.5 (CH), 129.0 (CH), 128.7 (CH), 127.0, 124.8 (CH), 124.0 (CH), 112.7, 112.5 (CH), 110.2 (CH), 106.6, 103.5 (CH), 97.9 (CH), 94.3 (CH$_2$), 84.5, 71.4 (CH), 56.1 (CH$_3$), 43.2 (CH$_2$), 36.0 (CH$_2$), 29.0 (CH$_2$), 28.7 (CH$_2$), 26.5 (CH$_2$), 25.0 (CH$_2$); LRMS (EI) m/z 427 (M$^+$-C$_4$H$_5$NO$_2$; 6), 181 (42), 129 (100); LRMS (FAB) m/z 526 (M$^+$); and HRMS (EI) for C$_{27}$H$_{25}$NO$_4$ (M$^+$-C$_4$H$_5$NO$_2$): the calculated molecular weight was 427.1784, and the found molecular weight was 427.1785.

Preparation of Example 8

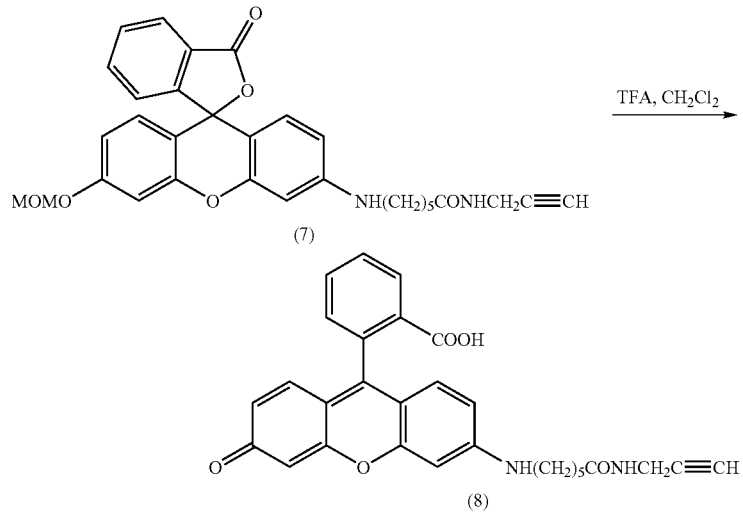

To a solution of Example 7 (53 mg, 0.1 mmol) in dry dichloromethane (CH$_2$Cl$_2$) (1 mL) was added trifluoroacetic acid (1 mL) dropwise at 0° C. The resulting solution was stirred at room temperature until the thin layer chromatography (TLC) indicated that all starting material was consumed. The mixture was concentrated under vacuo and then diluted with dichloromethane (CH$_2$Cl$_2$). The organic layer was washed with saturated sodium bicarbonate (NaHCO$_3$) solution and concentrated. The residue was then purified by silica gel column chromatography to give Example 8 (43 mg, 89% yield). Example 8 was characterized by the following spectroscopic data: $^1$H NMR (400 MHz, CD$_3$OD) δ 8.26 (dd, J=7.6, 1.0 Hz, 1H), 7.77-7.71 (m, 2H), 7.33 (dd, J=7.5, 1.0 Hz, 1H), 7.13-7.05 (m, 3H), 6.90-6.87 (m, 3H), 3.84 (d, J=2.5 Hz, 2H), 3.38 (t, J=7.0 Hz, 2H), 2.46 (t, J=2.5 Hz, 1H), 2.14 (t, J=7.3 Hz, 2H), 1.68-1.57 (m, 4H), 1.40-1.38 (m, 2H); $^{13}$C NMR (75.5 MHz, CD$_3$OD) δ 174.1, 167.2, 166.6, 161.6, 159.9, 156.8, 133.8, 132.6, 131.5, 131.2, 131.1, 130.8, 130.3, 129.9, 123.0, 118.8, 116.9, 116.0, 115.1, 101.9, 94.5, 79.2, 70.7, 43.2, 35.0, 28.0, 27.8, 26.0, 24.9; LRMS (FAB) m/z 483 ([M+H]$^+$); and HRMS (FAB) for C$_{29}$H$_{26}$N$_2$O$_5$ (M$^+$): the cal- -continued

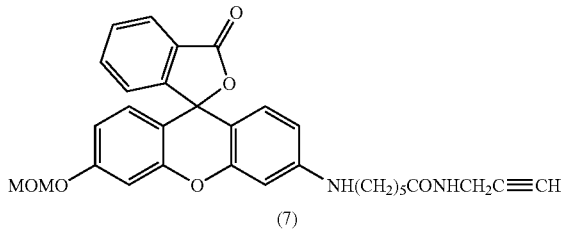

culated molecular weight was 482.1842, and the found molecular weight was 482.1830.

Example 9

In some embodiments, two or more of the rhodol fluorophores of formulae (III), (VI), (VIII), (IX), (XIII) and/or (XIV) disclosed herein can be used to form a library of rhodol fluorophores. In other embodiments, each rhodol fluorophore in the library has formula (VI). Some non-limiting examples of the rhodol fluorophore of formula (VI) are shown in Table 1 above. In certain embodiments, all or a part of the rhodol fluorophores shown in Table 1 form a library of rhodol fluorophores.

The photophysical properties of the rhodol fluorophores in Table 1 were measured according to the procedures disclosed herein and are summarized in Table 1. Stock solutions were prepared by accurately weighting and dissolving about 5-10 mg of the rhodol fluorophores in Table 1 in acetonitrile ($CH_3CN$). Absorbance solutions were prepared by further diluting the stock solution with 50 mM of potassium phosphate buffer at pH 8.0. Absorption spectra were recorded on a CARY 50 Bio UV-Visible spectrophotometer (obtainable from Varian Incorporation, Palo Alto, Calif.) under the control of a PC running the manufacturer supplied software package. Spectra were routinely acquired at 25° C., in 1 cm path length quartz cuvettes with a volume of 3.5 mL. Fluorescence spectra were recorded on a Hitachi F-2500 spectrofluorimeter (obtainable from Hitachi, Japan) under the control of a PC running the manufacturer supplied software package. Slit width was 2.5 nm for both the excitation spectrum and the fluorescence spectrum, and the photomultiplier voltage was 700 eV. All spectra were corrected for emission intensity using the manufacturer-supplied photomultiplier curves. The quantum yields of the fluorophores may be estimated by comparison of the integrated area of the corrected emission spectrum of the sample with that of a reference solution, such as a solution of rhodamine 6 G in water (quantum efficiency 0.76). The concentration of the reference was adjusted to match the absorbance of the test sample.

The purities of the rhodol fluorophores in Table 1 were measured according to the procedures disclosed herein and are summarized in Table 1. The purity of each of the rhodol fluorophores in Table 1 was determined by high performance liquid chromatography (HPLC) analysis of 10 µL aliquots of solutions containing the samples in methanol (MeOH). The high performance liquid chromatography (HPLC) analysis was performed with an Agilent 1100 HPLC system (obtainable from Agilent Technologies, Palo Alto, Calif.). The detector was set at 254 nm. Samples were eluted from an Alltima™ reverse-phase column (4.6×250 mm, C-18, 5 µm) with a gradient of water containing 0.1% of trifluoroacetic acid (TFA) and 2-98% of acetonitrile in 15 minutes at a flow rate of 1 mL/minute. Samples were detected by absorbance at 254 nm and the purity was calculated by integration of this absorbance.

The data in Table 1 show that, depending on the A, $R^1$ and $R^2$ groups of formula (III), the absorption maxima of the rhodol fluorophores in aqueous solution vary from approximately 490 to 560 nm and their extinction coefficients are generally not less than 47,000 $cm^{-1}M^{-1}$. Most of the rhodol fluorophores exhibit moderate to high quantum yields in phosphate buffer.

As demonstrated above, embodiments disclosed herein provide various rhodol compounds that can be used as for tracking detecting, measuring and/or screening biological species. While this disclosure has been described with respect to a limited number of embodiments, the specific features of one embodiment should not be attributed to other embodiments disclosed herein. No single embodiment is representative of all aspects of this disclosure. In some embodiments, the methods may include numerous compounds or steps not mentioned herein. In other embodiments, the methods do not include, or are substantially free of, steps not enumerated herein. Variations and modifications from the described embodiments exist. It is noted that the methods for making and using the rhodol compounds disclosed herein are described with reference to a number of steps. These steps can be practiced in any sequence. One or more steps may be omitted or combined but still achieve substantially the same results. The appended claims intend to cover all such variations and modifications as falling within the scope of this disclosure.

All publications and patent applications mentioned in this specification are herein incorporated by reference to the same extent as if each individual publication or patent application was specifically and individually indicated to be incorporated by reference. It is to be understood that this disclosure has been described in detailed by way of illustration and example in order to acquaint others skilled in the art with the invention, its principles, and its practical application. Further, the specific embodiments provided herein as set forth are not intended to be exhaustive or to limit the disclosure, and that many alternatives, modifications, and variations will be apparent to those skilled in the art in light of the foregoing examples and detailed description. Accordingly, this disclosure is intended to embrace all such alternatives, modifications, and variations that fall within the spirit and scope of the following claims. While some of the examples and descriptions above include some conclusions about the way the compounds, compositions and methods may function, the inventors do not intend to be bound by those conclusions and functions, but put them forth only as possible explanations in light of current understanding.

What is claimed is:

1. A rhodol compound having formula (VIII):

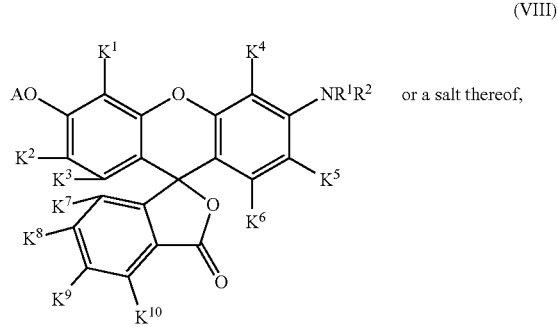

or a salt thereof, wherein A is H, alkyl, alkenyl, alkynyl, alkoxyalkyl, heteroalkyl, cycloalkyl, cycloalkenyl, cycloalkynyl, heterocyclyl, aminoalkyl, aryl, alkaryl, arylalkyl, carboxyalkyl, alkoxycarbonyl, acyl, aminocarbonyl, a hydroxy protecting group or a reactive functional group;

each of $R^1$ and $R^2$ is independently H, alkyl, alkenyl, alkynyl, alkoxyalkyl, heteroalkyl, cycloalkyl, cycloalkenyl, cycloalkynyl, heterocyclyl, aminoalkyl, aryl, alkaryl, arylalkyl, alkyloxy, carboxyalkyl, alkylamido, alkoxyamido, sulfonylaryl, acyl or a reactive functional group, wherein at least one of $R^1$, $R^2$, or $NR^1R^2$ comprises a reactive functional group;

each of $K^1$, $K^2$, $K^3$, $K^4$, $K^5$, $K^6$, $K^7$, $K^8$, $K^9$ and $K^{10}$ is independently H, halo, alkyl, halogenated alkyl, heteroalkyl, alkenyl, alkynyl, aryl, aralkyl, alkaryl, heterocyclyl, cycloalkyl, cycloalkenyl, cycloalkynyl, hydroxyalkyl, aminoalkyl, amino, alkylamino, arylamino, dialkylamino, alkylarylamino, diarylamino, acylamino, hydroxy, thiol, thioalkyl, alkoxy, alkylthio, alkoxyalkyl, aryloxy, arylalkoxy, acyloxy, cyano, nitro, sulfhydryl, carbamoyl, trifluoromethyl, phenoxy, benzyloxy, sulfonyl, phosphonyl, sulfonate ester, phosphate ester, —C(=O)—$P^1$ or —C(=O)—Q—$P^2$;

each of $P^1$ and $P^2$ is independently hydrogen, halo, alkoxy, hydroxy, thiol, alkyl, alkenyl, alkynyl, cycloalkyl, cycloalkenyl, cycloalkynyl, aryl, alkaryl, arylalkyl, carbamate, amino, alkylamino, arylamino, dialkylamino, alkylarylamino, diarylamino, alkylthio, heteroalkyl, or heterocyclyl having from 3 to 7 ring atoms; and Q is alkylene, alkenylene, alkynylene, arylene, aralkylene or alkarylene.

2. The rhodol compound of claim 1 wherein each of $K^1$, $K^2$, $K^3$, $K^4$, $K^5$, $K^6$, $K^7$, $K^8$, $K^9$ and $K^{10}$ is independently H.

3. The rhodol compound of claim 1, wherein each of $K^1$, $K^3$, $K^4$, $K^6$, $K^7$, $K^8$, $K^9$ and $K^{10}$ is independently H; and each of $K^2$ and $K^5$ is independently chlorine or fluorine.

4. The rhodol compound of claim 1, wherein each of $R^1$ and $R^2$ is alkyl.

5. The rhodol compound of claim 1, wherein $R^1$ is hydrogen; and $R^2$ is alkyl.

6. The rhodol compound of claim 1, wherein the reactive functional group is derived from acrylamide, acyl azide, acyl halide, nitrile, aldehyde, ketone, alkyl halide, alkyl sulfonate, anhydride, aryl halide, alkyne, alcohol, amine, carboxylic acid, carbodiimide, diazoalkane, epoxide, haloacetamide, hydroxylamine, hydrazine, imido ester, isothiocyanate, maleimide, sulfonate ester or sulfonyl halide.

7. The rhodol compound of claim 1, wherein the hydroxy protecting group is benzyloxycarbonyl, 4-nitrobenzyloxycarbonyl, 4-bromobenzyloxycarbonyl, 4-methoxybenzyloxycarbonyl, methoxycarbonyl, tert-butoxycarbonyl, isopropoxycarbonyl, diphenylmethoxycarbonyl, 2,2,2-trichloroethoxycarbonyl, 2-(trimethylsilyl) ethoxycarbonyl, 2-furfuryloxycarbonyl, allyloxycarbonyl, acetyl, formyl, chloroacetyl, trifluoroacetyl, methoxyacetyl, phenoxyacetyl, benzoyl, methyl, t-butyl, 2,2,2-trichloroethyl, 2-trimethylsilyl ethyl, 1,1-dimethyl-2-propenyl, 3-methyl-3-butenyl, allyl, benzyl, p-methoxybenzyldiphenylmethyl, triphenylmethyl (trityl), tetrahydrofuryl, methoxymethyl, methylthiomethyl, benzyloxymethyl, 2,2,2-triehloroethoxymethyl, 2- (trimethylsilyl)ethoxymethyl, methanesulfonyl, p-toluenesulfonyl, trimethylsilyl, triethylsilyl or triisopropylsilyl.

8. The rhodol compound of claim 1, having the following structure:

(8)

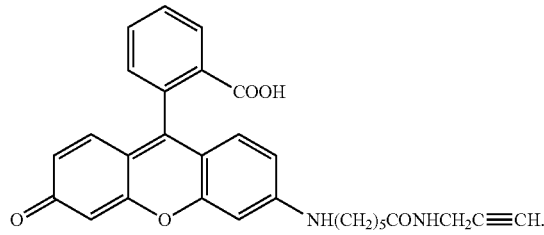

* * * * *

UNITED STATES PATENT AND TRADEMARK OFFICE
CERTIFICATE OF CORRECTION

PATENT NO. : 8,148,423 B2
APPLICATION NO. : 12/417640
DATED : April 3, 2012
INVENTOR(S) : Dan Yang and Tao Peng It is certified that error appears in the above-identified patent and that said Letters Patent is hereby corrected as shown below:

Column 6,
Line 16, "$R^4, K^5, K^2$" should read --$R^4, K^1, K^2$--.

Column 7,
Line 45, "2,2,2-triehloroethoxymethyl" should read --2,2,2-trichloroethoxymethyl--.

Column 8,
Line 27, "amino group" should read --amino groups--.

Column 11,
Lines 3-4, "2,2,2-triehloroethoxymethyl" should read --2,2,2-trichloroethoxymethyl--.
Line 26, "method" should read --method.--.

Column 14,
Line 13, "cross coupling" should read --cross-coupling--.
Lines 39-40, "cross coupling" should read --cross-coupling--.
Line 47, "$K^4$, K and" should read --$K^4, K^5$ and--.

Column 19,
Line 63, "cross coupling" should read --cross-coupling--.
Line 65, "cross coupling" should read --cross-coupling--.
Line 66, "cross coupling" should read --cross-coupling--.

Column 20,
Line 57, "cross coupling" should read --cross-coupling--.

Column 22,
Line 22, "$K^2, K^4, K^5, K^6, K^7, K^8, K^9, K^9$" should read --$K^2, K^3, K^4, K^5, K^6, K^7, K^8, K^9$--.

Signed and Sealed this
Tenth Day of July, 2012

David J. Kappos
*Director of the United States Patent and Trademark Office*

Column 29,
Line 49, "(M⁻; 23)" should read --(M⁺; 23)--.

Column 30,
Line 39, "(M⁻; 21)" should read --(M⁺; 21)--.

Column 33,
Line 2, "(M⁻); and" should read --(M⁺); and--.
Line 57, "were added" should read --was added--.

Column 34,
Line 5, "6.37 (1H)" should read --6.37 (s, 1H)--.

Column 35,
Line 65, "can be used as for tracking" should read --can be used for tracking,--.

Column 36,
Line 22, "in detailed by" should read --in detail by--.

Column 38,
Line 15, "2,2,2-triehloroethoxymethyl" should read --2,2,2-trichloroethoxymethyl--.